(12) United States Patent
MacDonald et al.

(10) Patent No.: US 12,228,561 B2
(45) Date of Patent: *Feb. 18, 2025

(54) SYSTEMS AND METHODS FOR INFERRING ENERGY AND BURNING PROPERTIES OF A FLUID IN A PIPELINE

(71) Applicant: MICRO MOTION, INC., Boulder, CO (US)

(72) Inventors: George Alexander MacDonald, Wokingham (GB); Tony Wright, Chichester (GB); Timothy James Pegg, Fleet (GB); Hans Christopher Loewenheath, Boulder, CO (US); Anthony William Pankratz, Arvada, CO (US)

(73) Assignee: MICRO MOTION, INC., Boulder, CO (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/762,503

(22) PCT Filed: Oct. 3, 2019

(86) PCT No.: PCT/US2019/054461
§ 371 (c)(1),
(2) Date: Mar. 22, 2022

(87) PCT Pub. No.: WO2021/066833
PCT Pub. Date: Apr. 8, 2021

(65) Prior Publication Data
US 2022/0349867 A1    Nov. 3, 2022

(51) Int. Cl.
*G01N 33/22*    (2006.01)
*G01N 9/00*    (2006.01)
*G01N 9/36*    (2006.01)

(52) U.S. Cl.
CPC .......... *G01N 33/225* (2013.01); *G01N 9/002* (2013.01); *G01N 9/36* (2013.01)

(58) Field of Classification Search
CPC .................. G01N 9/36; G01N 29/024; G01N 2291/0217; F23N 2221/10
See application file for complete search history.

(56) References Cited

U.S. PATENT DOCUMENTS

2017/0176402 A1* 6/2017 Pretre .................. G01N 33/225
2018/0306764 A1 10/2018 Huber et al.
(Continued)

FOREIGN PATENT DOCUMENTS

EP 3153854 A1 4/2017
JP H10281970 A * 10/1998
(Continued)

OTHER PUBLICATIONS

Machine Translation of JP 2006047071 A (Year: 2006).*
(Continued)

*Primary Examiner* — Nathaniel J Kolb
(74) *Attorney, Agent, or Firm* — The Ollila Law Group LLC

(57) ABSTRACT

A method for inferring energy content of a flow fluid in a gaseous state is disclosed. The method is carried out by a computer system (200) having a processor (210) and memory (220), the memory (220) having an inference module (204), the method comprising inferring, by the inference module (204), the inferred energy content of the flow fluid in the gaseous state from an inferential relationship between the inferred energy content of the flow fluid in the gaseous state with at least one measurement taken of the flow fluid in the liquid state.

7 Claims, 10 Drawing Sheets

(56) References Cited

U.S. PATENT DOCUMENTS

| | | | |
|---|---|---|---|
| 2019/0145327 A1 | | 5/2019 | Gieger et al. |
| 2019/0170723 A1 | | 6/2019 | Wheeler |
| 2019/0219556 A1 | * | 7/2019 | Buker .................. G01F 23/284 |
| 2019/0360990 A1 | | 11/2019 | Huber et al. |
| 2020/0041479 A1 | * | 2/2020 | Huber ..................... G01N 9/36 |
| 2020/0080984 A1 | * | 3/2020 | Ben Belgacem-Strek ................. F02M 21/0215 |
| 2022/0349797 A1 | * | 11/2022 | Macdonald ............. G01N 9/36 |

FOREIGN PATENT DOCUMENTS

| | | | |
|---|---|---|---|
| JP | 2006047071 A | * | 2/2006 |
| WO | 2016104270 A1 | | 6/2016 |

OTHER PUBLICATIONS

Machine Translation of JP H10281970 A (Year: 1998).*

Conor Slater et al, Validation of Novel Wobbe Index Sensor for Biogas Cogeneration, Solid State Phenomena, vol. 254, Aug. 30, 2016 (Aug. 30, 2016), pp. 43-48, XP055707618, DOI: 10.4028/www.scientific.net/SSP.254.43.

Lueptow R M et al, Acoustic sensor for determining combustion properties of natural gas, Measurement Science and Technology, IOP, Bristol, GB, vol. 5, No. 11, Nov. 1, 1994 (Nov. 1, 1994), pp. 1375-1381, XP020065812, ISSN: 0957-0233, DOI: 10.1088/0957-0233/5/11/010.

Christof Huber et al, Gas Density and Viscosity Measurement With a Microcantilever and Determination of Wobbe Index, Calorific Value and Total Inert Gas Content of Natural Gas, Oct. 6, 2017, pp. 156-159, XP055695340, Retrieved from Internet: URL:https://www.researchgate.net/profile/Christof_Huber/publication/320282829_Gas_density_and_viscosity_measurement_with_a_microcantilever_and_determination_of_Wobbe_index_calorific_value_and_total_inert_gas_content_of_natural_gas/links/5a213031a6fdcc6a18bbd3d5/Gas-density-and-viscosity-measurement-with.

(Continuation of Non-Patent Literature Documents No. 3 above): [retrieved on May 14, 2020].

* cited by examiner

SYSTEMS AND METHODS FOR INFERRING ENERGY AND BURNING PROPERTIES OF A FLUID IN A PIPELINE

TECHNICAL FIELD

The embodiments described below relate to energy content determinations, more particularly, to inferential energy content determinations.

BACKGROUND

Liquefied natural gas (hereinafter, "LNG") is becoming an increasingly important fuel because the high energy content makes it efficient for transportation. LNG is natural gas which has been processed and liquefied by cooling to a low temperature. An example of typical transportation conditions is at a temperature of about −162° C. and 126.3 kilopascals (absolute). The composition of LNG differs significantly from source to source and based on the processing applied to the LNG. Typical compositions may include nitrogen, methane, ethane, propane, and higher order hydrocarbons (with four or more carbons in the chain). Due to the variation in composition, it is difficult to know the energy content and burning properties of the different LNG mixtures at the point of delivery. LNG composition can greatly affect the value of the LNG mixtures, and it is necessary to assess the LNG content before purchase.

The current practice for determining energy content of discharged LNG is to measure the volume of LNG and calculate the mean density and mean calorific value from a composition analysis from a gas chromatograph. A common equation used is Eq. (1):

$$E_{LNG} = V_{LNG} \times \delta_{LNG} \times H_{LNG} \quad (1)$$

In Eq. (1), $V_{LNG}$ is the volume of LNG measured in the LNG Carrier's tanks, $\delta_{LNG}$ is the density of LNG calculated based on the chromatographic analysis and temperature of LNG, and $H_{LNG}$ is the mean mass-based Gross Calorific Value (GCV) of LNG calculated through chromatographic analysis of LNG.

As can be seen, existing systems require the use of chromatographs to determine relative composition of the gases. Gas chromatographs take significant time to make determinations, as the sampling and analysis process is slow. Further, chromatography is expensive and cannot be performed in real time. During the time it takes to analyze a sample, the composition of the flowing LNG could change dramatically, making the chromatographic determinations impractical for purposes of determining energy content of the LNG being assessed. Typical LNG and other liquid line measurements include simpler parameters, such as density, viscosity, pressure, and speed of sound (hereinafter, "SOS"). Measurement of these parameters is more practical on-line. However, these measurements are not direct measurements of energy content. Inferential determinations are ones in which there is not a direct relationship between the parameters being measured and the variable being calculated from the measured parameters. If typical fluid measurements taken at line conditions could be applied to inferential relationships to infer energy content, the resulting inferences could benefit from greater sampling rate and recency. The process would also benefit from avoiding costly sampling and chromatography procedures.

Accordingly, there is a need for systems that use inferential relationships with typical LNG measurements to determine live energy content values.

SUMMARY

Embodiments of methods for inferring energy content of a flow fluid in a gaseous state are disclosed. The method may be carried out by a computer system (200) having a processor (210) and memory (220), the memory (220) having an inference module (204), the method comprising inferring, by the inference module (204), the inferred energy content of the flow fluid in the gaseous state from an inferential relationship between the inferred energy content of the flow fluid in the gaseous state with at least one measurement taken of the flow fluid in the liquid state.

Embodiments of apparatuses for inferring energy content of a flow fluid in a gaseous state are disclosed. The apparatus has a computer system (200), the computer system (200) having a processor (210) and memory (220), the memory (220) having an inference module (204), the inference module (204) configured to infer the inferred energy content of the flow fluid in the gaseous state from an inferential relationship between the inferred energy content of the flow fluid in the gaseous state with at least one measurement taken of the flow fluid in the liquid state.

Aspects

According to an aspect, a method for inferring energy content of a flow fluid in a gaseous state is disclosed. The method may be carried out by a computer system (200) having a processor (210) and memory (220), the memory (220) having an inference module (204), the method comprising inferring, by the inference module (204), the inferred energy content of the flow fluid in the gaseous state from an inferential relationship between the inferred energy content of the flow fluid in the gaseous state with at least one measurement taken of the flow fluid in the liquid state.

Preferably, the at least one measurement comprises a measured density.

Preferably, the at least one measurement further comprises one or more of a measured viscosity and a measured speed of sound.

Preferably, the inferential relationship is a sum of terms, wherein each term has one or more of one of the at least one measurement and one higher order value of one of the at least one measurement.

Preferably, each term has a coefficient that corresponds to the term.

Preferably, each coefficient is temperature dependent, wherein each coefficient temperature dependency has at least one term-specific coefficient constant.

Preferably, the relationship has at least five terms, the at least five terms comprises a shift term, a measured density term having the measured density, a higher order density term having a higher order value of the measured density, at least one of a measured viscosity term and a speed of sound term correspondingly having the one or more of the measured viscosity and the measured speed of sound, and at least one of a higher order viscosity term or a higher order speed of sound term correspondingly having one or more of a higher order value of the one or more of the measured viscosity and the measured speed of sound.

Preferably, the flow fluid is a natural gas mixture.

Preferably, the energy content is one of methane number, lower flammability limit, Wobbe Index, gross heating value, and net heating value.

Preferably, the computer system (200) is a meter electronics (110) of a vibratory sensor (102), the vibratory sensor (102) measuring one or more of the at least one measurement.

According to an aspect, an apparatus for inferring energy content of a flow fluid in a gaseous state is disclosed. The apparatus has a computer system (200), the computer system (200) having a processor (210) and memory (220), the memory (220) having an inference module (204), the inference module (204) configured to infer the inferred energy content of the flow fluid in the gaseous state from an inferential relationship between the inferred energy content of the flow fluid in the gaseous state with at least one measurement taken of the flow fluid in the liquid state.

Preferably, the at least one measurement comprises a measured density.

Preferably, the at least one measurement further comprises one or more of a measured viscosity and a measured speed of sound.

Preferably, the inferential relationship is a sum of terms, wherein each term has one or more of one of the at least one measurement and one higher order value of one of the at least one measurement.

Preferably, each term has a coefficient that corresponds to the term.

Preferably, each coefficient is temperature dependent, wherein each coefficient temperature dependency has at least one term-specific coefficient constant.

Preferably, the relationship has at least five terms, the at least five terms comprising a shift term, a measured density term having the measured density, a higher order density term having a higher order value of the measured density, at least one of a measured viscosity term and a speed of sound term correspondingly having the one or more of the measured viscosity and the measured speed of sound, and at least one of a higher order viscosity term or a higher order speed of sound term correspondingly having one or more of a higher order value of the one or more of the measured viscosity and the measured speed of sound.

Preferably, the flow fluid is a natural gas mixture.

Preferably, the energy content is one of methane number, lower flammability limit, Wobbe Index, gross heating value, and net heating value.

Preferably, the apparatus is a vibratory sensor (102), wherein the computer system (200) is a meter electronics (110) of the vibratory sensor (102), the vibratory sensor (102) measuring one or more of the at least one measurement.

BRIEF DESCRIPTION OF THE DRAWINGS

The same reference number represents the same element on all drawings. It should be understood that the drawings are not necessarily to scale.

DETAILED DESCRIPTION

Figure 1:
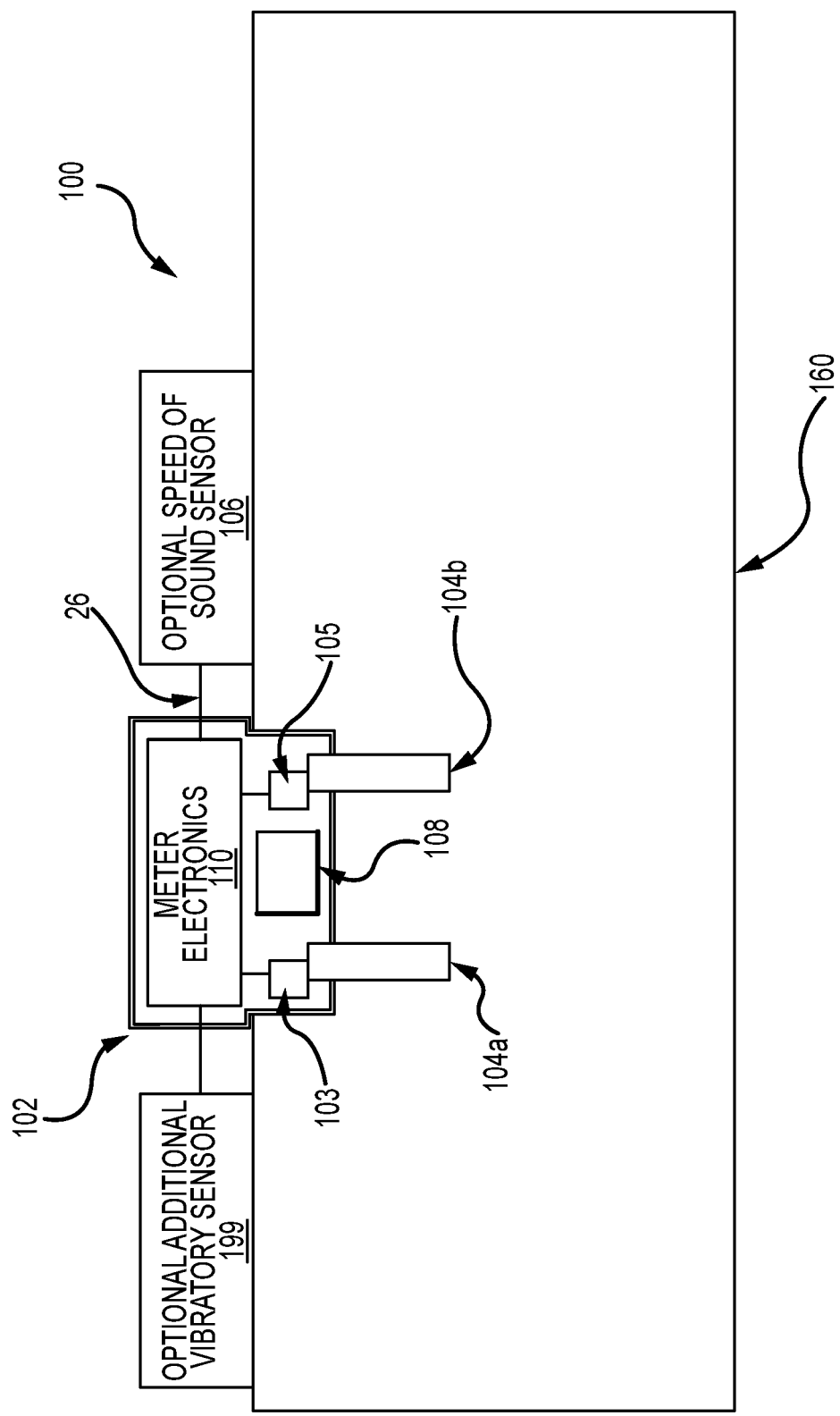
FIG. 1 shows a block diagram of an embodiment of a flow fluid measuring system.

FIGS. 1-10 and the following description depict specific examples to teach those skilled in the art how to make and use the best mode of embodiments of inferring energy content. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of energy content inferences. As a result, the embodiments described below are not limited to the specific examples described below, but only by the claims and their equivalents.

When isolating the type of fluid to particular classes, for instance, natural gas mixtures, it can be seen that simple relationships between typically measured quantities in fluid flow arrangements can be used to infer energy content of the fluids. This is especially true if the measurements and inferential relationship are determined based on quantities in the liquid state in order to infer the energy content in the gaseous state. When the terms "infer" or "inferring" are used in verb form, it should be understood that this means to determine using inferential associations, for instance, using inferential relationships. This inferring can be done without any direct measurements of heat related metrics, for instance, thermal conductivity, heat capacity, and thermal diffusivity. Further, the inferring can be done without other traditional considerations for determining energy content, such as permittivity, laminar resistances, turbulent resistances, and refractive index. Also, the inferring can be done without artificially generating temperature and/or pressure drops across the measurement equipment beyond those temperature and pressure drops associated with typical flow measurement device interactions with the fluid.

Because these relationships are relatively simple for specific classes of gases, for instance, natural gas mixtures, the inferential relationships may be represented as linear combinations of the simple measurements in the liquid state with associated coefficients. For instance, the inferential relationship may be so simple that it merely accounts for measurement(s) of the fluid in the liquid state, perhaps at line conditions. The relationship may incorporate a corresponding coefficient for the measurement of the fluid in the liquid state. In an embodiment, the corresponding coefficient may have a temperature dependent relationship such that the corresponding coefficient varies with measured temperature of the fluid in the liquid state. In an embodiment, each of the measured values of the liquid in the fluid state (except, potentially, temperature) that are used in the inferential relationship, may have a different corresponding temperature dependent coefficient. It should be noted that, despite the mixture being called natural "gas," natural gas mixtures in both the liquid (i.e. LNG) and gaseous states are contemplated when using the term, natural gas. It should be noted that the specification is not limited to natural gas mixtures and may apply to other classes of fluid with energy content that may be in the liquid and gaseous states.

The inferential relationship may further have a shift term (A) that serves as a reference value relationship for the energy content. The shift term may also be temperature dependent ($K_1(T)$). In an embodiment, one of the measured values of the fluid in the liquid state is a measured density of the fluid in the liquid state. The measured density may be an element of a density term (B) of the inferential relationship. The density term (B) may be a product of the measured density and the corresponding coefficient for the measured density. In an embodiment, the relationship may be a sum of the shift term and the density term.

In another embodiment, the measured values of the fluid in the liquid state may further include a measured speed of sound of the fluid in the liquid state. The relationship may further account for the measured speed of sound. For instance, the relationship may further have a speed of sound term that incorporates the measured speed of sound. In this embodiment, the speed of sound term may be the measured speed of sound multiplied by a corresponding coefficient that corresponds to the speed of sound. In an embodiment, the relationship may be a sum of the shift term, the density term, and the speed of sound term. In still other embodiments, the speed of sound may be substituted with a viscosity measurement. For instance, the relationship may have a viscosity term that incorporates the measured viscosity. In this embodiment the viscosity term may be the measured viscosity multiplied by a corresponding coefficient that corresponds to the measured viscosity. In an embodiment, the relationship may be a sum of the shift term, the density term, and the viscosity term.

Relationships in which one measured quantity of the fluid in the liquid state that is not a measured temperature is incorporated may take the form of Eq. (2)

$$IEC_{Gas}=A+B \tag{2}$$

In Eq. (2), the $IEC_{Gas}$ is the inferred energy content value of the fluid in gaseous form. A is a shift term. B is a density term, as shown here, but it should be appreciated that other measured terms may be used instead in Eq. (2).

In all embodiments, the shift term (A) may be expressed as a constant or may be expressed as a temperature dependent quantity ($K_1(T)$), perhaps having a simple relationship with temperature, as shown in Eq. (3):

$$A=K_1(T) \tag{3}$$

The density term (B) may be expressed as a product of a measured density of the fluid in a liquid state ($\rho_{liquid}$) with a coefficient that corresponds to the measured density ($K_2$), as shown in Eq. (4):

$$B=K_2 \times \rho_{liquid} \tag{4}$$

In an embodiment, the coefficient that corresponds to the measured density ($K_2$) may be a temperature dependent coefficient ($K_2(T)$), such that Eq. (4) becomes Eq. (5).

$$B=K_2(T) \times \rho_{liquid} \tag{5}$$

In an embodiment, Eq. (2) may take the form of Eq. (6)

$$IEC_{Gas}=K_1(T)+K_2(T) \times \rho_{liquid} \tag{6}$$

It should be appreciated that embodiments where some or all of the coefficients and shift term are constants and do not vary with temperature.

In an embodiment in which more than one measured quantity of the fluid in the liquid state (the more than one measured quantity not including a measured temperature in the terms but having coefficients potentially dependent upon temperature) is used in the inferential relationship, the inferential relationship may take the form of equation (7):

$$IEC_{Gas}=A+B+C \tag{7}$$

The shift term (A) and the density term (B) may be as expressed in Eqs. (3) to (6). In an embodiment where the speed of sound of the fluid in the liquid state is one of the more than one measured quantity used in the inferential relationship, the relationship may have a speed of sound term (C), as shown in Eq. (7).

The speed of sound term (C) may be expressed as a product of a measured speed of sound of the fluid in the liquid state ($SOS_{liquid}$) with a coefficient that corresponds to the measured speed of sound ($K_3$), as shown in Eq. (8):

$$C=K_3 \times SOS_{liquid} \tag{8}$$

In an embodiment, the coefficient that corresponds to the measured speed of sound ($K_3$) may be a temperature dependent coefficient ($K_3(T)$), such that Eq. (8) becomes Eq. (9).

$$C=K_3(T) \times SOS_{liquid} \tag{9}$$

In an embodiment, the relationship expressed in Eq. (7) may be expressed as Eq. (10).

$$IEC_{Gas}=K_1(T)K_2(T) \times \rho_{liquid} K_3(T) \times SOS_{liquid} \tag{10}$$

In various embodiments in which more than one measured quantity of the fluid in the liquid state (the more than one measured quantity not including a measured temperature in the terms, but having coefficients potentially dependent upon temperature), a viscosity measurement of the fluid in the liquid state may be used instead of or in addition to the speed of sound. In this embodiment, a viscosity term (D) might be used in addition to or instead of the speed of sound term (C).

The viscosity term (D) may be expressed as a product of a measured viscosity of the fluid in the liquid state ($\eta_{liquid}$) with a coefficient that corresponds to the measured viscosity ($K_4$), as shown in Eq. (11):

$$D=K_4 \times \eta_{liquid} \tag{11}$$

In an embodiment, the coefficient that corresponds to the measured viscosity ($K_4$) may be a temperature dependent coefficient ($K_4(T)$), such that Eq. (11) becomes Eq. (12).

$$D=K_4(T) \times \eta_{liquid} \tag{12}$$

In an embodiment, the inferential relationship may be a sum that incorporates a viscosity term (D) with a density term (B) and a shift term (A) and not a speed of sound term (C) as shown in Eq. (13):

$$IEC_{Gas}=A+B+D \tag{13}$$

In an embodiment, the relationship of Eq. (13) may be expressed as Eq. (14).

$$IEC_{Gas}=K_1(T)+K_2(T) \times \rho_{liquid}+K_4(T) \times \eta_{liquid} \tag{14}$$

In still another embodiment, all of the shift term (A), density term (B), speed of sound term (C), and viscosity term (D) may be accounted for in the inferential relationship. For instance, the inferential relationship may be a sum of the shift term (A), density term (B), speed of sound term (C), and viscosity term (D), as shown in Eq. (15).

$$IEC_{Gas}=A+B+C+D \tag{15}$$

In an embodiment, the relationship of Eq. (13) may be expressed as Eq. (16).

$$IEC_{Gas}=K_1(T)+K_2(T)\times\rho_{liquid}K_3(T)\times SOS_{liquid}K_4(T)\times\eta_{liquid} \quad (16)$$

The inferential relationship may further account for any number of terms (hereinafter, "higher order terms") with squared or higher order exponentials of measured parameters used (hereinafter, "higher order measurements"), for instance, squares or higher order exponentials of one or more of measured density of the fluid in the liquid state, measured speed of sound of the fluid in the liquid state, and viscosity of the fluid in the liquid state. The inferential relationship may have corresponding coefficients for each of the higher order measurements. The corresponding coefficients of the higher order measurements may each have temperature dependencies. The higher order measurements may be represented in the inferential relationships in higher order terms. In various embodiments, the higher order terms may be products of each higher order measurement and each corresponding coefficient. One or more higher order terms may be incorporated into the inferential relationships as further sums, for instance, further sums of the higher order terms that would be added to the right side of any of Eqs. (2), (6), (7), (10), (13), (14), (15), and (16).

In an embodiment, the inferential relationship may be quadratic in certain terms and may take the form of Eq. (17):

$$IEC_{Gas}=K_1(T)+K_2(T)\times\rho_{liquid}+K_5(T)\times\rho^2_{liquid}+K_4(T)\times\eta_{liquid}+K_6(T)\times\eta^2_{liquid} \quad (17)$$

In Eq. (17) $K_5(T)$ and $K_6(T)$ are temperature dependent coefficients for squared density and squared viscosity measurement values respectively. An alternative embodiment is contemplated where the coefficients are constants that do not vary with temperature (ie. $K_1$-$K_6$ are constants). This provides quadratic relationships between each of density and viscosity with the inferred energy content of a gas.

In an embodiment each of the terms of the inferential relationship may only have one of a measured value and a higher order measured value.

The temperature dependency of one or more of the temperature dependent coefficients (e.g. $K_1(T)$, $K_2(T)$, $K_3(T)$, $K_4(T)$, $K_5(T)$, and/or $K_6(T)$) can be determined by any number of relationships. For instance, the relationship between a coefficient and temperature could be linear, an embodiment of which is shown in Eq. (18):

$$K_x(T)=G+H\times T \quad (18)$$

In Eq. (18) G and H are constants (hereinafter, "coefficient constants") that can be determined by analysis means, for instance, regression, over several different gas mixtures at different ranges of temperatures. Each term may have a temperature dependent coefficient, and each temperature dependency of the coefficient may have at least one term-specific coefficient constant (e.g. G and/or H may be term-specific coefficient constants for the exemplary "$x^{th}$" term in Eq. (19)). The "x" subscript is merely to denote that the coefficient relationship described in Eq. (18) is generic to any corresponding measurement value (or higher order measurement value, e.g. squared measured density) in the inferential relationship. "Relationship elements" may include one or more of the coefficients and coefficient constants. For the purposes of the specification, if a structure of inferential relationship is determined, the structure for instance of the form of one or more Eqs. (2)-(19), the inferential relationship may be characterized by this structure and relationship elements.

In another embodiment, the temperature dependency of one or more of the temperature dependent coefficients (e.g. $K_1(T)$, $K_2(T)$, $K_3(T)$, $K_4(T)$, $K_5(T)$, and/or $K_6(T)$) can be determined by a quadratic relationship with temperature, an embodiment of which is shown in Eq. (19):

$$K_x(T)=G+H\times T+I\times T^2 \quad (19)$$

In Eq. (19), G, H, and I may be constants that can be determined by analysis means, for instance, regression, over several different gas mixtures at different ranges of temperatures. Again, the "x" subscript is merely to denote that the coefficient relationship described in Eq. (19) is generic to any corresponding measurement value (or higher order measurement value) in the inferential relationship. Each of the temperature dependent coefficients (e.g. $K_1(T)$, $K_2(T)$, $K_3(T)$, $K_4(T)$, $K_5(T)$, and/or $K_6(T)$) may have different values of one or more of G, H, and I and/or may have different ordered polynomials in temperature for each of the coefficients such that more or fewer coefficients are used. One or more of the relationships expressed in Eqs. (2)-(19) could be used to infer values of one or more of MN, a LFL, a WI, a GHV, and a NHV from typical measurements taken at line conditions.

Examples of these implementations are shown in FIGS. 6-10 and their corresponding descriptions.

It should be appreciated that embodiments where some or all of the coefficients and shift term are constants and do not vary with temperature.

FIG. 1 shows a block diagram of an embodiment of a flow fluid measuring system. The system 100 has a vibratory sensor 102, an optional speed of sound sensor 106, and an optional additional vibratory sensor 199. It should be appreciated that any vibratory sensor 102 system could be used, for instance, a Coriolis flow meter, a fork densitometer, a fork viscometer, and/or the like. The same applies to the optional vibratory sensor 106. In various embodiments, multiple vibratory sensors 102 of the same or different types may be used in series to determine measurements to be used in inferential determinations of energy content.

The vibratory sensor 102 and/or 199 can be used to provide typical flow fluid and/or fluid flow measurements of a fluid that interacts with the vibratory sensor. Typical measurements provided by vibratory sensors 102 and/or 199 may include, for instance, one or more of density, viscosity, speed of sound, mass flowrate, and volumetric flowrate of a fluid in a liquid state. The vibratory sensor 102 and the optional additional vibratory sensor 199 may be different types of vibratory sensors, such that they are structured differently and/or may provide different measurements from one another. For instance, the vibratory sensor 102 may be a fork viscosity meter and the optional additional vibratory sensor 199 may be a Coriolis flow sensor. This is merely exemplary, and all variations of potential flow sensors 102 and/or combinations of flow sensors 102 and optional additional flow sensors 199 are contemplated.

The vibratory sensor 102 and/or 199 may be mounted in a pipe or conduit, a tank, a container, or other fluid vessels. The vibratory sensor 102 and/or 199 can also be mounted in a manifold or similar structure for directing a fluid flow. However, other mounting arrangements are contemplated and are within the scope of the description and claims.

In an embodiment, the vibratory sensor 102 and/or 199 may be a fork meter, for instance a fork viscosity meter or a fork density meter. The vibratory sensor 102 and/or 199 may have a meter electronics 110, a driver 103, a first tine 104a, a second tine 104b, a response sensor 105, a temperature sensor 108, and a communication link 26. The vibratory sensor 102 operates to provide fluid measurements. The vibratory sensor 102 may provide fluid measurements including, for instance, one or more of a fluid density (ρ), fluid temperature (T), a fluid viscosity (η), a mass flowrate, a volumetric flowrate, and a pressure (P) for a fluid, including flowing or non-flowing fluids. This listing is not exhaustive, and the vibratory sensor 102 and/or 199 may measure or determine other fluid characteristics.

The meter electronics 110 is a processing circuit that processes raw signal data for taking measurements and/or processing programming modules. The meter electronics 110 may be an embodiment of the computer 200 shown in FIG. 2. The meter electronics 110 controls operation of the driver 103 and the response sensor 105 of the vibratory sensor 102 and can provide electrical power to the driver 103 and the response sensor 105. For example, the meter electronics 110 may generate a drive signal and provide the generated drive signal to the driver 103 to generate vibrations in the first tine 104a. The first tine 104a is an immersed element of the vibratory sensor 102. The generated drive signal can control the vibrational amplitude and frequency of the first tine 104a. The generated drive signal can also control the vibrational duration and/or vibrational timing. It should be noted that the meter electronics 110 may represent multiple components and products that are used in unison but perhaps sold separately. For instance, the meter electronics 110 may comprise electronics of the meter and the electronics of other communicably coupled elements, for instance, a transmitter or other device the use of which requires the meter and its electronics.

The driver 103 is an element that drives motions. The first tine 104a is an element that is vibrated and interacts with a fluid. The driver 103 may receive drive signals from the meter electronics 110 to vibrate the first tine 104a. The second tine 104b is another immersed element that has a resulting vibration, perhaps driven by the vibration of the first tine 104a. The second tine 104b is coupled to a response sensor that measures the vibratory response of the second tine 104b, such that the relationship between the vibratory response of the second tine 104b and the driver signal applied to the driver 103 that drives the first tine 104a, is representative of properties of the fluid. These vibrations may be driven to allow for flow fluid and/or fluid flow measurements to be determined by the meter electronics 110. The temperature sensor 108 is a device that measures temperature. Fluid flow and/or fluid flow measurements may have temperature dependencies, so the temperature sensor 108 may provide temperature data to the meter electronics 110 for use in the measurements.

The meter electronics 110 can receive a vibration signal or signals from a response sensor 105 that detects motion and/or vibrations of the second tine 104b. In an embodiment, the meter electronics 110 may drive the vibratory element in a phase lock, such that the command signal provided to the driver 103 and the response signal received from the response sensor 105 are phase locked. The meter electronics 110 may process the vibration signal or signals to generate a density (ρ) measurement, for example. The meter electronics 110 processes the vibration signal or signals received from the response sensor 105 to determine a frequency of the signal or signals. Further, or in addition, the meter electronics 110 processes the vibration signal or signals to determine other characteristics of the fluid, such as a viscosity (η). In alternative embodiments, the meter electronics 110 may also determine a phase difference between upstream and downstream signals, that can be processed to determine a fluid flow rate, for example. As can be appreciated, the phase difference is typically measured or expressed in spatial units such as degrees or radians although any suitable unit can be employed such as time-based units. If time-based units are employed, then the phase difference may be referred to by those in the art as a time delay between the vibration signal and the drive signal. Other vibrational response characteristics and/or fluid measurements are contemplated and are within the scope of the description and claims.

The meter electronics 110 can be further coupled to a communication link 26. The meter electronics 110 may communicate the vibration signal over the communication link 26. The meter electronics 110 may also process the received vibration signal to generate a measurement value or values and may communicate the measurement value or values over a communication link 26. In addition, the meter electronics 110 can receive information over the communication link 26. For example, the meter electronics 110 may receive commands, updates, operational values or operational value changes, and/or programming updates or changes over the communication link 26. In various embodiments, the communication link 26 may be an embodiment of or communicatively coupled to a communicative coupler 240.

The vibratory sensor 102 and/or 199 may provide a drive signal for the driver 103 using a closed-loop circuit. The drive signal is typically based on the received vibration signal. The closed-loop circuit may modify or incorporate the vibration signal or parameters of the vibration signal into the drive signal. For example, the drive signal may be an amplified, modulated, or an otherwise modified version of the received vibration signal. The received vibration signal can therefore comprise a feedback that enables the closed-loop circuit to achieve a target frequency or phase difference. Using the feedback, the closed-loop circuit incrementally changes the drive frequency and monitors the vibration signal until the target phase is reached, such that the drive frequency and vibration signal are phase locked at or near the target phase.

Fluid properties, such as the viscosity (η) and density (ρ) of the fluid, can be determined from the frequencies where the phase difference between the drive signal and the vibration signal is 135° and 45°. These desired phase differences, denoted as first off-resonant phase difference $\phi 1$ and second off-resonant phase difference $\phi 2$, can correspond to the half power or 3 dB frequencies. The first off-resonant frequency $\omega 1$ is defined as a frequency where the first off-resonant phase difference $\phi 1$ is 135°. The second off-resonant frequency $\omega 2$ is defined as a frequency where the second off-resonant phase difference $\phi 2$ is 45°. Density (ρ) measurements made at the second off-resonant frequency $\omega 2$ can be independent of fluid viscosity (η). Accordingly, density (ρ) measurements made where the second off-resonant phase difference $\phi 2$ is 45° can be more accurate than density (ρ) measurements made at other phase differences.

In some embodiments, the vibratory sensor 102 may only determine one of the density (ρ) and viscosity (η) with another implement determining the other of the density (ρ) and viscosity (η), the other implement perhaps being a different vibratory meter.

Various embodiments of the vibratory sensor 102 are contemplated, and the embodiment shown in FIG. 1 is merely for exemplary purposes. Any vibratory sensor 102 may be used, for instance, the fork meter described or a Coriolis flow sensor.

The optional speed of sound sensor 106 is a sensor that detects the speed of sound of a fluid. The optional speed of sound sensor 106 may determine a speed of sound of a fluid in a liquid state to determine the energy content of the fluid in the gaseous state. The optional speed of sound sensor 106 may transmit a sound, using a sound transmitter, through the liquid fluid to be measured and receive, with a sonic sensor, the response. The speed of sound may then be determined based on the time of transit and the distance between the sound transmitter and the sonic sensor. This is merely exemplary and other methods of measuring speed of sound by the optional speed of sound sensor 106 are contemplated.

Although not depicted, one or more of the vibratory sensors 102 and/or 199 may be a Coriolis flow sensor. Coriolis flow sensors may determine phase differences in measured oscillations due to Coriolis forces to determine mass flowrate and/or density of a fluid, perhaps a fluid in a liquid state and/or a fluid in a gaseous state. In an embodiment, neither of the vibratory sensor 102 and the optional additional vibratory sensor 199 are fork meters (such that the vibratory sensor 102 shown in FIG. 1 is different from the vibratory sensor 102 of this embodiment). In another embodiment, the vibratory sensor 102 may be a gas density meter that relies on vibrating. The manners in which vibratory sensor(s) 102 and/or 199 and optional speed of sound sensors 106 measure and determine measured quantities is well-established in the art, and further disclosure is omitted for brevity.

A computer system, for instance, a meter electronics 110 of the vibratory sensor 102, may be configured to use one or more typical flow fluid and/or fluid flow measurements to infer a value of an energy content metric for the fluid in the gaseous state, for instance, using any of the relationships expressed in Eqs. (2) to (19) and other examples taught by this specification.

Examples of typical energy content metrics include methane number (hereinafter, "MN"), lower flammability limit (hereinafter, "LFL"), Wobbe Index (hereinafter, "WI"), gross heating value (hereinafter, "GHV"), and net heating value (hereinafter, "NHV"). In the embodiments disclosed in this specification, the inferred energy content may be one or more of a MN, a LFL, a WI, a GHV, and a NHV.

MN is an energy content measurement that may represent the knock potential of a fluid when combusted. It describes a likelihood that the fuel will combust uncontrollably. An embodiment of a relationship to find MN is shown in Eq. (20):

$$MN = \\ -119.1 + 1.464\left(-406.14 + 508.04\left(\frac{H}{C}\right) - 173.55\left(\frac{H}{C}\right)^2 + 20.17\left(\frac{H}{C}\right)^3\right) \quad (20)$$

In Eq. (19), MN is methane number and $$\left(\frac{H}{C}\right)$$

is atomic hydrogen to carbon ratio (e.g.

$$\left(\frac{H}{C}\right)$$

for methane is tour tor methane which has four hydrogens and one carbon). To determine this directly, one would have to know the composition of a fluid mixture, something difficult to determine at line conditions.

LFL is an energy content measurement that represents the minimum composition of the gas in a mixture with air at which combustion will occur. An embodiment of a relationship to find LFL is shown in Eq. (21):

$$LFL = \frac{1}{\sum_i \frac{x_i}{LFL_i}} \quad (21)$$

In Eq. (21), LFL is the lower flammability limit, i is an index referencing each component of the mixture, $x_i$ is the relative proportion of the component i, and $LFL_i$ is a lower flammability limit of the component i. Methods using this relationship are limited by needing to know composition. Composition can be difficult to determine at line conditions.

WI is an energy metric that represents interchangeability of fuel gases. The WI is a calorific value relative to the root of the specific gravity. Eq. (22) shows an embodiment of a relationship for determining WI:

$$WI = \frac{C_V}{\sqrt{SG}} \quad (22)$$

In Eq. (22), WI is Wobbe Index, $C_V$ is calorific value, and SG is specific gravity of the fluid. Again, traditional measurements for determining calorific value require knowing relative composition of the mix and require a composition determination. Composition determinations may be impractical when determining or inferring live measurements at line conditions.

GHV and NHV are both heating values, often referred to as calorific values. The difference between GHV and NHV is that NHV is reduced by the amount of heat that would result from condensing any water vapor in the mixture. An embodiment of a method for determining GHV is shown in Eq. (23):

$$GHV_V = [(1571.5 \times SG) + 144] - (25.318 \times \% \, CO_2 + 16.639 \times \% \, N_2) \quad (23)$$

In Eq. (23), $GHV_V$ is the gross heating value (in volume units), % $CO_2$ is carbon dioxide composition of the mix by volume and % $N_2$ is nitrogen composition of the mix by volume. Eq. (23) is the AGA 5 equation relationship in volumetric units. It should be noted that only terms for carbon dioxide and nitrogen are shown, but more elements exist in the equation for other substances which are omitted for brevity. In some systems, Eq. (23) yields calorific value in BTU per cubic foot at 14.73 pounds per square inch pressure and 60° F.

A mass unit equivalent of the AGA 5 equation may also be used. An embodiment of the mass unit equivalent is shown in Eq. (23A):

$$GHV_M = .02035 + \frac{(0.001970 - ((M_C \times 0.000329) + (M_N \times 0.000217)))}{SG} \quad (23A)$$

In Eq. (23A), $GHV_M$ is the gross heating value (in mass units), $M_C$ is carbon dioxide composition by mass, $M_N$ is nitrogen composition by mass, and SG is specific gravity.

To get NHV, one could use the resulting GHV of either of Eqs. (23) or (23A) and subtract from it the heat of condensation of any water vapor of the mix. Again, this will require a composition determination. Composition determinations may be impractical when determining or inferring live measurements at line conditions.

In an embodiment in which the inferential relationship does not depend on velocity of sound of a fluid in a liquid state, a single vibratory meter 102, perhaps a fork viscosity meter (hereinafter, "FVM") may be used to determine the inferred energy content of a fluid in a gas state based on measurements taken of the fluid in a liquid state. The measurements taken by the FVM may include a measured density and a measured viscosity. These measured quantities taken of the fluid in the liquid state may be used to infer energy content of the fluid in a gaseous state. In an embodiment in which a FVM (e.g. vibratory sensor 102) is used, a separate Coriolis flow sensor (e.g. optional additional vibratory sensor 199) may still be used to determine mass flowrate of a fluid in a liquid state. When both mass flowrate and energy content are determined by any of the systems disclosed in this specification, the systems may further derive from the mass flowrate and the energy content of a fluid in a liquid state an energy flowrate of a fluid, such that the flow of a fluid in a liquid state is measured in energy the fluid flowing can provide in a gaseous state per unit time.

In another embodiment, the inferential relationship does depend on measured speed of sound of a fluid in the liquid state. In this embodiment, an optional speed of sound sensor 106 may be used to determine the speed of sound of a fluid in a liquid state. In an embodiment in which the speed of sound of a fluid in a liquid state is used and a density of a fluid in a liquid state is used, the speed of sound measurements of a fluid in a liquid state determined by the optional speed of sound sensor 106 may be transmitted to another computer, perhaps a meter electronics of a vibratory sensor 102 and/or 199, in order to infer an energy content of the fluid in a gaseous state in the another computer. In this embodiment, one or more of a density and a viscosity of a fluid in a liquid state may be determined by the vibratory sensor 102 and/or 199 and used with the transmitted speed of sound measurement of a fluid in a liquid state to infer the energy content of the fluid in a gaseous state.

Further embodiments are envisioned in which multiple vibratory sensors 102 and/or 199 are each used to measure one or more of mass flowrate, density, and viscosity of a fluid in a liquid state, and/or the optional speed of sound sensor 106 is used to measure the speed of sound of a fluid in a liquid state. All combinations of potential hardware and software arrangements based on the types of sensors disclosed and the measurements potentially used in the inference of energy content are contemplated by this specification.

Figure 2:
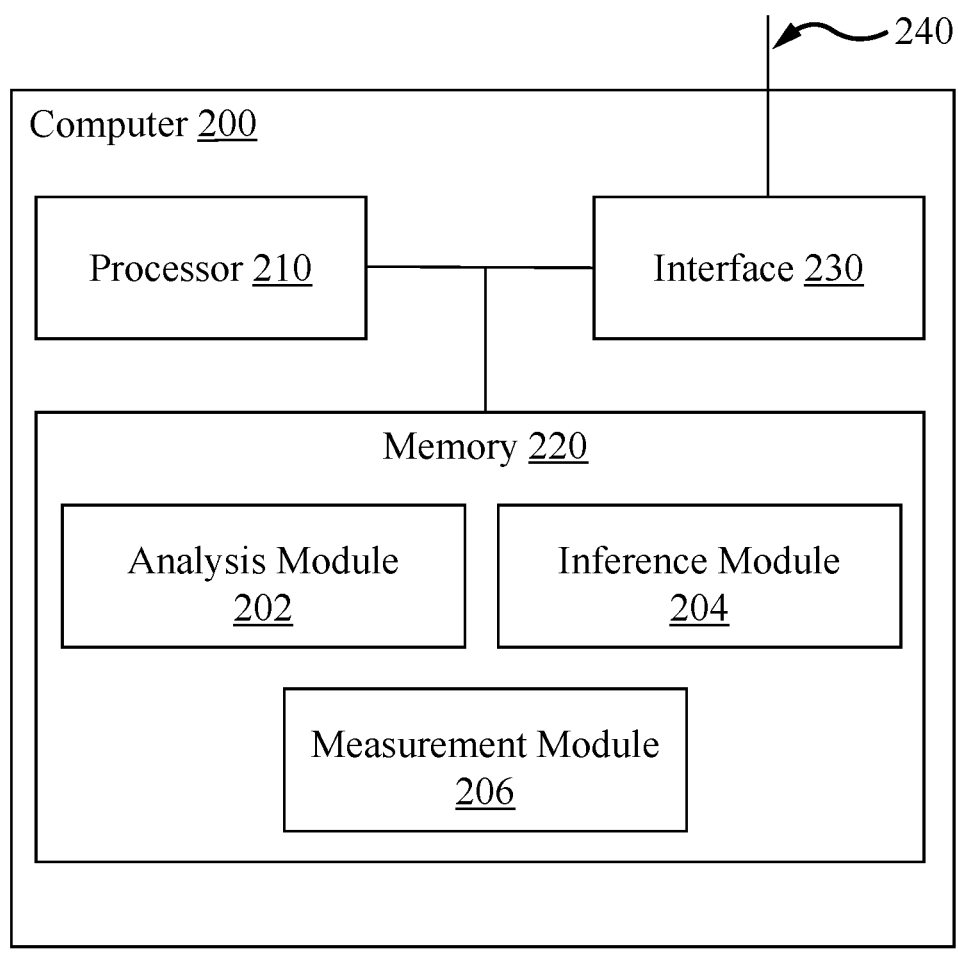
FIG. 2 shows a block diagram of an embodiment of a computer system 200.

FIG. 2 shows a block diagram of an embodiment of a computer system 200. In an embodiment, the computer system 200 may be a meter electronics, for instance, the meter electronics 110. In various embodiments the computer system 200 may be comprised of application specific integrated circuits or may have a discrete processor and memory elements, the processor elements for processing commands from and storing data on the memory elements. The computer system 200 may be an isolated physical system, a virtual machine, and/or may be established in a cloud computing environment. The computer system 200 may be configured to accomplish any method steps presented in this description and may execute all functions associated with the disclosed modules.

The computer system may have a processor 210, a memory 220, an interface 230, and a communicative coupler 240. The memory 220 may store and/or may have integrated circuits representing, for instance, an analysis module 202, an inference module 204, and a measurement module 206. In various embodiments, the computer system 200 may have other computer elements integrated into the stated elements or in addition to or in communication with the stated computer elements, for instance, buses, other communication protocols, and the like.

The processor 210 is a data processing element. The processor 210 may be any element used for processing such as a central processing unit, application specific integrated circuit, other integrated circuit, an analog controller, graphics processing unit, field programmable gate array, any combination of these or other common processing elements and/or the like. The processor 210 may have cache memory to store processing data. The processor 210 may benefit from the methods in this specification, as the methods may enhance the resolution of calculations and reduce error of those calculations using the inventive structures presented.

The memory 220 is a device for electronic storage. The memory 220 may be any non-transitory storage medium and may include one, some, or all of a hard drive, solid state drive, volatile memory, integrated circuits, a field programmable gate array, random access memory, read-only memory, dynamic random-access memory, erasable programmable read-only memory, electrically erasable programmable read-only memory, cache memory and/or the like. The processor 210 may execute commands from and utilize data stored in the memory 220.

The computer system 200 may be configured to store any data that will be used by the analysis module 202, the inference module 204, and the measurement module 206 and may store historical data for any amount of time representing any parameter received or used by the analysis module 202, the inference module 204, and the measurement module 206 in the memory 220, perhaps with time stamps representing when the data was taken or determined. The computer system 200 may also store any data that represents determinations of any intermediates in the memory 220. While the analysis module 202, the inference module 204, and the measurement module 206 are displayed as three separate and discrete modules, the specification contemplates any number (even one or the three as specified) and variety of modules working in concert to accomplish the methods expressed in the specification.

The analysis module 202 is a programming module that determines an inferential relationship between an energy content of a fluid in a gaseous state and parameters of the fluid measured while the fluid is in a liquid state. The analysis module 202 may use any methods and equations disclosed in this specification to determine the inferential relationship, for instance, the methods disclosed in the description of FIG. 1 and Eqs. (2)-(19). The analysis module may determine, using an evaluation procedure, for instance, regression or a machine learning algorithm, the inferential relationship using existing data. For instance, analysis may be performed on various relationships that incorporate various measured parameters of a fluid in a liquid state and converge the resulting inferred energy content to known, measured energy content of the fluid in a gaseous state. For instance, the analysis module 202 may receive data representing one or more of measured density of the fluid in the liquid state, measured speed of sound of the fluid in the liquid state, and/or measured viscosity of the fluid in the liquid state and corresponding measured values of energy content of the same fluid in the gaseous state and determine values of inferential relationship elements in the inferential relationship that relate the measured parameters of the fluid in the liquid state to the measured energy content values of the same fluid in the gaseous state. In various embodiments, the inferential relationship will have elements that are temperature dependent such that the determination of the inferential relationship, by the analysis module 202, also requires receiving values of measured temperature of the fluid in a liquid state, the measured temperature perhaps taken contemporaneously or substantially contemporaneously with the other measured values. Inferential relationship elements may include measured parameters, higher powers of measured parameters, coefficients (perhaps corresponding coefficients that correspond to one or more of measured parameters or higher powers of the measured parameters), temperature dependencies of various coefficients, and/or the like. The inferential relationship may be described by one or more of Eqs. (2)-(19), and the analysis module may use one or more of the relationships expressed in Eqs. (2)-(19) to determine the inferential relationship. The analysis module 202 may further use equations with higher order terms of measurement values (for instance, quadratic terms) to determine the inferential relationship, as taught in this specification.

The analysis module 202 may use only some measured values to determine the inferential relationship. For instance, in an embodiment, the analysis module 202 may receive a measured quantity value of a fluid in a liquid state to determine a term that corresponds with the measured quantity (e.g. A, B, C, and/or D). The analysis module 202 may incorporate temperature measurements of the fluid in a liquid state to establish temperature dependency of coefficients and, perhaps a shift term (A). In this embodiment, the analysis module 202 may determine a corresponding coefficient that corresponds to the measured quantity value and multiply the measured quantity value by the corresponding coefficient that corresponds to the measured quantity value to generate a term that corresponds to the measured quantity value. The analysis module 202 may conduct an evaluation procedure to determine the coefficient that corresponds to the measured value using the measured quantity value of the fluid in the liquid state and a measured energy content of the fluid in a gaseous state. In an embodiment, the corresponding coefficient and/or the shift term is temperature dependent, such that the corresponding coefficient and/or the shift term is not a constant. In this embodiment, the analysis module 202 may determine, by the evaluation procedure, the relationship between the measured temperature of the fluid in the liquid state and the corresponding coefficient and/or the shift term.

The analysis module 202 may use different inferential relationships for each of the types of inferred energy content, depending on which measurements and terms are appropriate for each of the types of inferred energy content. For instance, one or more of a measured density, measured temperature, measured viscosity, measured speed of sound, higher order values of measurements, and the like may be used in the inferential relationship. The measuring of one or more measured quantities used in determining elements of the inferential relationship (for instance, coefficient constants) may be accomplished by the system 100 using the computer system 200, and/or the computer system 200 may receive the measured data from sources that have already determined measurements and corresponding measured energy content values.

The analysis module 202 may determine or receive from a user an inferential relationship with elements, for instance, the structure of the inferential relationship (e.g. relationships expressed by Eqs. (2)-(19)) and relationship elements (e.g. coefficients, coefficient constants, and temperature and/or pressure dependent relationships to determine coefficients, potentially ones reflected in the relationships expressed in Eqs. (2)-(19)). The coefficients and/or coefficient constants of the Eqs. and/or the elements used to determine the coefficients may be determined by the analysis module 202, for instance, using a regression or other statistical or probabilistic technique. The structure of the inferential relationship may be determined by the analysis module 202 (e.g. may determine best relationship for each energy content metric) or may be supplied by the user or meter electronics 110. The resulting inferential relationship elements may be associated by the analysis module 202 with one or more of the energy metric being determined, the flow fluid, and a class of flow fluids of which the flow fluid is a member. The data regarding the one or more of the energy metric, fluid type, and fluid class may be supplied by a user or may be determined and/or identified by the analysis module 202. The resulting inferential relationship, relationship elements, and data associations therewith may be stored in the computer system 200 that determined the inferential relationship with the analysis module 202 or may be transmitted to a different computer system 200, perhaps a meter electronics 110 of a vibratory sensor 102 (or directly coupled hardware).

The inference module 204 uses the inferential relationship having predetermined elements (for instance, predetermined relationships between terms and/or predetermined coefficient constants) to infer inferred energy content values. The inferential relationship stored may have predetermined and/or prestored elements, for instance, the structure of the inferential relationship (e.g. relationships expressed by Eqs. (2)-(19)) and relationship elements (e.g. coefficients, coefficient constants, and temperature and/or pressure dependent relationships to determine coefficients, potentially ones reflected in the relationships expressed in Eqs. (2)-(19)). The coefficients of the Eqs. and/or the elements used to determine the coefficients may be predetermined and prestored in the computer system 200 (or directly coupled hardware). The inferential relationship elements may be associated by data with one or more of the energy metric being determined, the flow fluid, and a class of flow fluids of which the flow fluid is a member. The data regarding the one or more of the energy metric, fluid type, and fluid class may be supplied by a user or may be determined and/or identified by the inference module 204. The data associations may assure that the inference module 204 uses the best inferential relationship elements and energy content metric for a particular application. The inference module 204 may retrieve, from memory 220, the appropriate relationship elements for the particular flow fluid and application. From this the inference module 204 may evaluate the inferential relationship to determine the energy content of a fluid in a gaseous state from measurements taken of the fluid in the liquid state.

In an embodiment, it should be appreciated that the determination of elements of the inferential relationship (for instance, predetermined relationships between terms and/or predetermined coefficient constants) may be conducted by a first system, and the predetermined elements determined in that first system may be used in live inferences of energy content in a second system. In this embodiment, the computer system 200 for the first system may have one or more of the analysis module 202 and the measurement module 206, but not have the inference module 204. In this embodiment, the computer system 200 for the second system may have one or more of the inference module 204 and the measurement module 206, but not have the analysis module 202.

In another embodiment, a computer system 200 may be used to both determine the elements of the inferential relationship (for instance, predetermined relationships between terms and/or predetermined coefficient constants) and deploy the inferential relationship to infer energy content values from live line condition measurements. In this embodiment, the computer system 200 may have one or more of the analysis module 202, inference module 204, and the measurement module 206.

The measurement module 206 is a programming module that takes raw data from sensors and processes the raw data to determine flow fluid and/or fluid flow measurements. The flow fluid and/or flow fluid measurements may include one or more of measured density, pressure, viscosity, speed of sound, temperature, mass flowrate, and/or the like. In various embodiments, various hardware elements may be incorporated into the system. Each of the different hardware elements in system 100 may have different embodiments of the measurement module 206. For instance, the vibratory sensor 102 may measure one or more of density and viscosity, using an embodiment of the measurement module 206. The optional speed of sound sensor 106 may measure speed of sound of the flow fluid using its own embodiment of the measurement module 206. The optional additional vibratory sensor 199 may determine mass and/or volumetric flowrate of the flow fluid using its own embodiment of measurement module 206.

The capabilities of the analysis module 202, the inference module 204, and the measurement module 206 are contemplated and reflect the methods that are performed in the flowcharts presented. All methods in this specification are contemplated with respect to each flowchart and orders specified or, when it is specified that the order does not matter, inform the flowcharts, but all methods and capabilities of the analysis module 202, the inference module 204, and the measurement module 206 are contemplated for the purposes of any method claims that follow this description.

Also, in embodiments where the computer system 200 is a meter electronics 110, the meter electronics 110 may comprise a number of communicatively coupled elements. The hardware that interacts to form the cohesive computer system 200 that is the meter electronics 110 may be of different components, for instance, a traditional meter electronics array communicatively coupled to a corresponding and/or compatible transmitter. In an embodiment, the meter electronics 110 may have at least some elements of its processor 210 in the integral meter electronics elements of the vibratory sensor 102 and at least some elements of the memory 220 in the transmitter coupled to the vibratory sensor 102.

The interface 230 is an input/output device used to communicatively couple the data computer system 200 to external compute elements. The interface 230 is capable of connecting the computer system 200 to external elements, using known technologies, the external elements including, for instance, universal serial bus, Prolink, serial communication, serial advanced technology attachments, HPC type connections, Gigabit Ethernet, infiniband, and/or the like. The interface 230 may have a communicative coupler 240. The communicative coupler 240 is used to couple the computer system 200 with components external of the computer system 200, for instance, with external compute devices or facilitating data transfer between one or more of the vibratory sensor 102, the optional speed of sound sensor 106, and the optional additional vibratory sensor 199. In an embodiment in which the computer system 200 is a meter electronics 110 comprised of multiple compatible and potentially separably couplable elements (e.g. traditional meter electronics of a vibratory sensor 102 and a transmitter), the communicative coupler 240 may communicatively couple the elements. In an embodiment, the communicative coupler 240 may be an embodiment of the communication link 26.

Flowcharts

Figure 3:
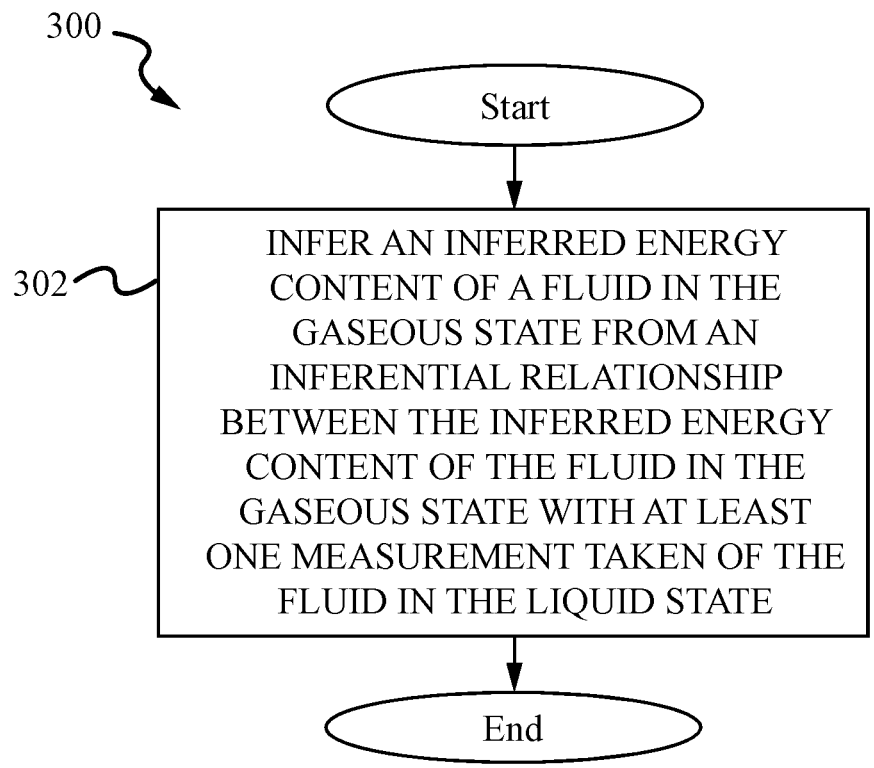
FIG. 3 shows a flowchart of an embodiment of a method 300 for inferring an energy content.
Figure 4:
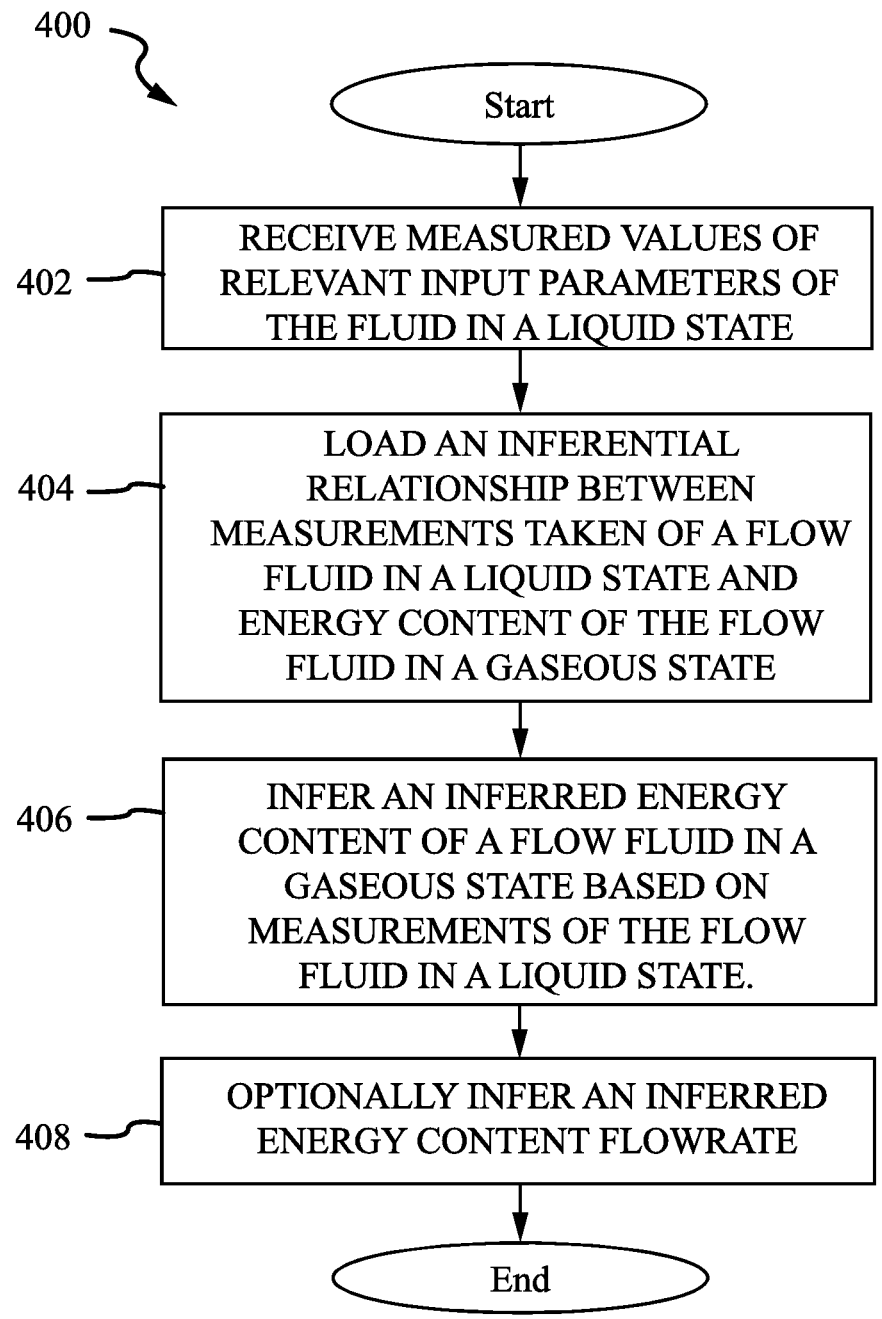
FIG. 4 shows a flowchart of an embodiment of a method 400 for inferring an energy content.
Figure 5:
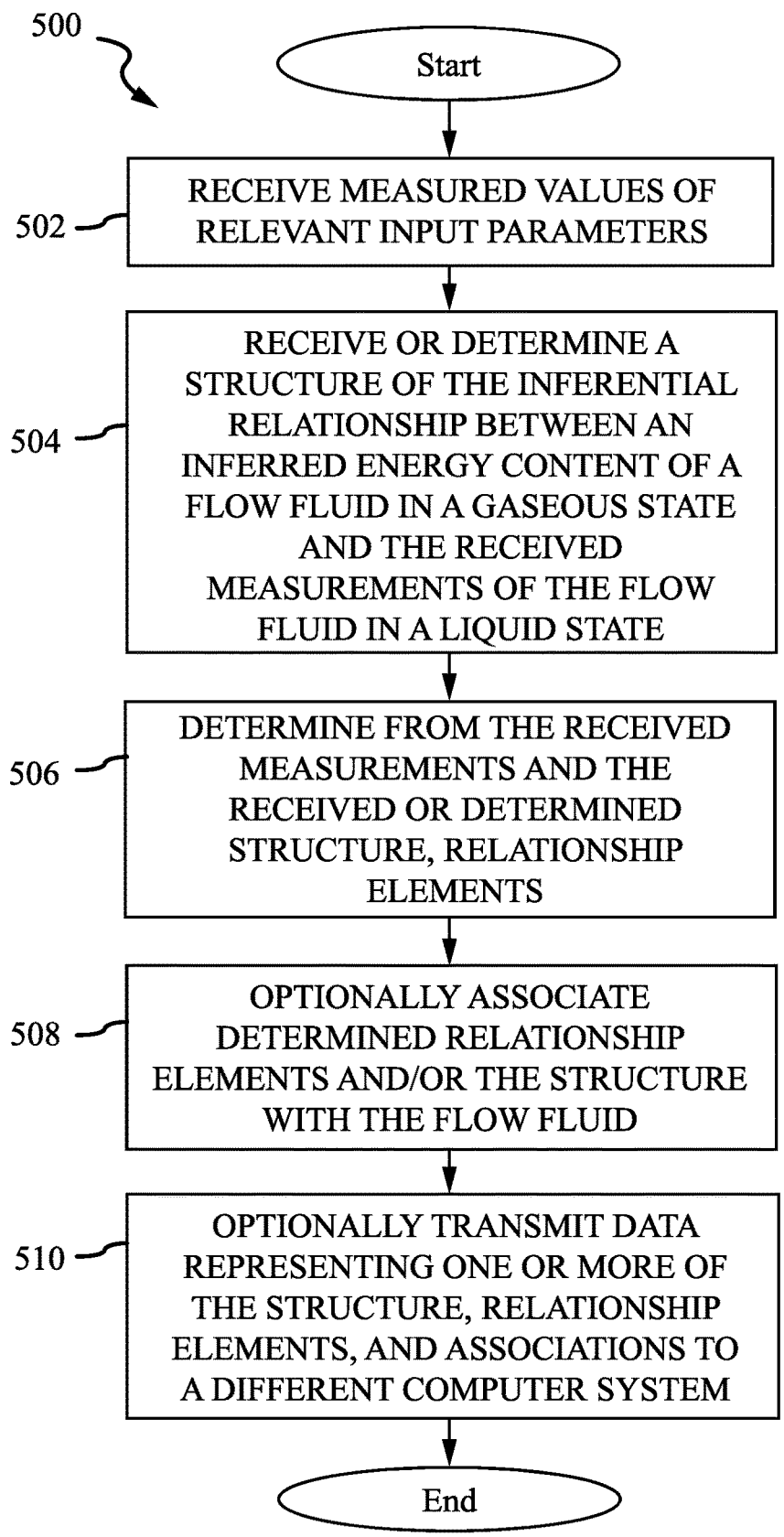
FIG. 5 shows a flowchart of an embodiment of a method 500 for inferring an energy content.

FIGS. 3-5 show flowcharts of embodiments of methods for inferring and using an energy content. The methods disclosed in the flowcharts are non-exhaustive and merely demonstrate potential embodiments of steps and orders. The methods must be construed in the context of the entire specification, including elements disclosed in descriptions of FIGS. 1 and 2, system 100 and computer system 200 disclosed in FIGS. 1 and 2, the analysis module 202, inference module 204, and/or measurement module 206.

FIG. 3 shows a flowchart of an embodiment of a method 300 for inferring an energy content. The system 100, vibratory sensor 102, optional speed of sound sensor 106, optional additional vibratory sensor 199, computer system 200, analysis module 202, inference module 204, and measurement module 206 referred to or implicitly used in method 300 may be the system 100, vibratory sensor 102, optional speed of sound sensor 106, optional additional vibratory sensor 199, computer system 200, analysis module 202, inference module 204, and measurement module 206 referred to in method 300 as disclosed in FIGS. 1 and 2, although any suitable system 100, vibratory sensor 102, optional speed of sound sensor 106, optional additional vibratory sensor 199, computer system 200, analysis module 202, inference module 204, and measurement module 206 referred to or implicitly used in method 300 may be employed in alternative embodiments. All methods for accomplishing these steps disclosed in this specification are contemplated, including all of the capabilities of the system 100.

Step 302 is inferring, by the inference module 204, an inferred energy content of a fluid in the gaseous state from an inferential relationship between the inferred energy content of the fluid in the gaseous state with at least one measurement taken of the fluid in the liquid state. Step 302 may be conducted by an inference module 204 of a vibratory sensor 102 and/or an optional additional vibratory sensor 199. The inferring may be based on relationships expressed in one or more of Eqs. (2)-(19). The values of the input parameters for the inference may be provided by one or more of the vibratory sensor 102, the optional speed of sound sensor 106, and the optional additional vibratory sensor 199.

In other embodiments, the method shown in FIG. 3 may have other steps in addition to or instead of the step listed above. Subsets of the step listed above as part of the method shown in FIG. 3 may be used to form their own method. The step of method 300 may be repeated in any combination and order any number of times, for instance, continuously looping in order to provide live or continuous line condition inferred energy content values.

FIG. 4 shows a flowchart of an embodiment of a method 400 for inferring an energy content. The system 100, vibratory sensor 102, optional speed of sound sensor 106, optional additional vibratory sensor 199, computer system 200, analysis module 202, inference module 204, and measurement module 206 referred to or implicitly used in method 400 may be the system 100, vibratory sensor 102, optional speed of sound sensor 106, optional additional vibratory sensor 199, computer system 200, analysis module 202, inference module 204, and measurement module 206 referred to in method 400 as disclosed in FIGS. 1 and 2, although any suitable system 100, vibratory sensor 102, optional speed of sound sensor 106, optional additional vibratory sensor 199, computer system 200, analysis module 202, inference module 204, and measurement module 206 referred to or implicitly used in method 400 may be employed in alternative embodiments. All methods for accomplishing these steps disclosed in this specification are contemplated, including all of the capabilities of the system 100. Method 400 may be an embodiment of step 302, and step 302 may be an embodiment of method 400.

Step 402 is receiving, by an inference module 204, measured values of relevant input parameters of the fluid in a liquid state. In an embodiment, the relevant input parameters may be one or more of density, viscosity, temperature, pressure, and speed of sound. In an embodiment, the inference module 204 may be stored in the vibratory sensor 102. The vibratory sensor 102 may use its own measurement module 206 to measure quantities, for instance, one or more of density, viscosity, and temperature of the flow fluid. The vibratory sensor 102 may receive a measured speed of sound from the optional speed of sound sensor 106 if the embodiment of the inferential relationship calls for use of a speed of sound quantity. In an embodiment, the vibratory sensor 102 may optionally receive a mass flowrate from the optional additional vibratory sensor 199.

Step 404 is loading, by the inference module 204, an inferential relationship between measurements taken of a flow fluid in a liquid state and inferred energy content of the flow fluid in a gaseous state. The inferential relationship stored in the meter electronics 110 may have predetermined and/or prestored elements, for instance, the structure of the inferential relationship (e.g. relationships expressed by Eqs. (2)-(19)) and relationship elements (e.g. coefficients, coefficient constants, and temperature and/or pressure dependent relationships to determine coefficients, potentially ones reflected in the relationships expressed in Eqs. (2)-(19)). The coefficients of the Eqs. and/or the elements used to determine the coefficients may be predetermined and prestored in the meter electronics 110 of the vibratory sensor 102 (or directly coupled hardware). One or more of these inferential elements may have been determined in a previously executed method, for instance, an embodiment of the method 500 as shown in FIG. 5. These elements may have been established in a different computer system with an analysis module 202. These coefficients, structures and/or elements may be specific to one or more of the flow fluid or the class of fluids of which the flow fluid is a member, for instance, by the computer system 200 having data stored that represents an association between at least one of the coefficients, coefficient constants, structures, and/or elements and the one or more of the flow fluid and the class of which the flow fluid is a member. The loading may entail the user specifying the flow fluid or the class of fluids of which the flow fluid is a member and loading the associated data representing the inferential relationship. For instance, the inferential relationship may be associated with natural gas mixtures to be used in inferences of natural gas mixture energy contents. In an alternative embodiment, the vibratory sensor 102 may be a fixed purpose meter for a particular fluid or class of fluids with the inferential relationship loaded for the specific fluid. In still another embodiment, the meter electronics 110 may dynamically identify the flow fluid and apply the appropriate inferential relationship associated with one or more of the flow fluid identified, the class of fluids of which the flow fluid is a member, and the energy content metric to be used for the particular application.

Step 406 is inferring, by the inference module 204, an inferred energy content of a flow fluid in a gaseous state based on measurements of the flow fluid in a liquid state. The inferring may use an inferential relationship, for instance, a prestored and/or predetermined relationship. The inferential relationship may be based on one or more of the relationships shown in Eqs. (2)-(19). The inference module 204 may use any of the capabilities of the inference module 204 taught in this specification to accomplish the inferring of Step 406. Step 406 may be an embodiment of step 302 and/or method 300.

Step 408 is optionally inferring, by the inference module 204, an inferred energy content flowrate. Much like a mass or volumetric flowrate, an energy content flowrate can be determined by determining an energy content with a basis (the basis typically being one or more of mass or volume) and applying it to a flowrate in the basis. For instance, if the basis is mass, an energy content may be inferred that is based on a unit of mass and that inferred energy content per unit mass can be applied to a measured mass flowrate in order to yield an inferred energy content flowrate.

In an embodiment, each of the steps of the method shown in FIG. 4 is a distinct step. In another embodiment, although depicted as distinct steps in FIG. 4, steps 402-408 may not be distinct steps. In other embodiments, the method shown in FIG. 4 may not have all of the above steps and/or may have other steps in addition to or instead of those listed above. The steps of the method shown in FIG. 4 may be performed in another order. Subsets of the steps listed above as part of the method shown in FIG. 4 may be used to form their own method. The steps of method 400 may be repeated in any combination and order any number of times, for instance, continuously looping in order to provide live or continuous line condition inferred energy content values.

FIG. 5 shows a flowchart of an embodiment of a method 500 for inferring an energy content. The system 100, vibratory sensor 102, optional speed of sound sensor 106, optional additional vibratory sensor 199, computer system 200, analysis module 202, inference module 204, and measurement module 206 referred to or implicitly used in method 500 may be the system 100, vibratory sensor 102, optional speed of sound sensor 106, optional additional vibratory sensor 199, computer system 200, analysis module 202, inference module 204, and measurement module 206 referred to in method 500 as disclosed in FIGS. 1 and 2, although any suitable system 100, vibratory sensor 102, optional speed of sound sensor 106, optional additional vibratory sensor 199, computer system 200, analysis module 202, inference module 204, and measurement module 206 referred to or implicitly used in method 500 may be employed in alternative embodiments. All methods for accomplishing these steps disclosed in this specification are contemplated, including all of the capabilities of the system 100.

Step 502 is receiving, by an analysis module 202, measured values of relevant input parameters. In an embodiment, the relevant input parameters may be one or more of density, viscosity, temperature, pressure, energy content (perhaps of a fluid in a gaseous state), and speed of sound. In an embodiment, the inference module 204 may be stored in the vibratory sensor 102. The vibratory sensor 102 may use its own measurement module 206 to measure quantities, for instance, one or more of density, viscosity, and temperature of the flow fluid. The vibratory sensor 102 may receive a measured speed of sound from the optional speed of sound sensor 106 if the embodiment of the inferential relationship calls for use of a speed of sound quantity.

Step 504 is receiving or determining, by the analysis module 202, a structure of the inferential relationship between an inferred energy content of a flow fluid in a gaseous state and the received measurements of the flow fluid in a liquid state. The analysis module 202 may have stored a user supplied preferred structure for the inferential relationship, or the analysis module 202 may optimize and determine the best structure for the inferential relationship by trying a variety of different structures of the inferential relationships and determining which is best based on comparison of the results (perhaps by conducting this method multiple times with different flow fluids for determining optimal structure of relationships specific to the flow fluid or a class of fluid of which the flow fluid is a member). Exemplary structures of the inferential relationship are shown in Eqs. (2)-(19).

Step 506 is determining, by the analysis module 202, from the received measurements and the received or determined structure, relationship elements. These relationship elements may include the coefficients and coefficient constants of relationships expressed by relationships represented by one or more of Eqs. (2)-(19). These relationship elements may be specific to the flow fluid or to a class of fluids of which the flow fluid is a member or to which the flow fluid is otherwise related. Step 506 may be the core of the determination of the inferential relationship. The determined inferential relationship may be characterizable by the structure and the relationship elements, perhaps for a given fluid. Step 506 may use a regression or other analysis technique conducted on a structure into which the measured values are entered. The analysis may be used to determine the relationship elements that best allow the inferential relationship having the selected structure, using the measured values of inputs, to converge the inferred energy content output by the inferential relationship to a measured energy content of the fluid in a gaseous state that corresponds to the actual measured values input. By converging the measured energy content of the fluid in the gaseous state to the inferred energy content produced by the inferential relationship based on measurements taken of the fluid in the liquid state, the relationship elements may be determined that can be used in later energy content inferences.

Step 508 is optionally associating, by the analysis module 202, determined relationship elements and/or the structure with the flow fluid. Further associations may be included, for instance, associations with relationships for the energy content metric being used. The associations may be stored in the computer system 200 in such a way that the relationship elements and/or the structure is associated with one or more of the flow fluid, a class of fluids of which the flow fluid is a member or to which the flow fluid is related, and/or the particular energy content metric used. The data representing one or more of the relationship elements and the structure may be stored and/or associated with data identifying one or more of the flow fluid, an associated class of fluids, or the energy metric used. The association may be stored in memory 220.

Step 510 is optionally transmitting, by the analysis module 202, data representing one or more of the structure, relationship elements, and associations to a different computer system 200. The different computer system 200 may be one that does not have the analysis module 202. The different computer system 200 may be a meter electronics 110 of a vibratory sensor 102. The different computer system 200 may use this data as predetermined and/or prestored data to make inferences of energy content of the flow fluid, perhaps even live inferences thereof.

In an embodiment, each of the steps of the method shown in FIG. 5 is a distinct step. In another embodiment, although depicted as distinct steps in FIG. 5, steps 502-510 may not be distinct steps. In other embodiments, the method shown in FIG. 5 may not have all of the above steps and/or may have other steps in addition to or instead of those listed above. The steps of the method shown in FIG. 5 may be performed in another order. Subsets of the steps listed above as part of the method shown in FIG. 5 may be used to form their own method. The steps of method 500 may be repeated in any combination and order any number of times, for instance, continuously looping in order to provide live or continuous line condition inferred energy content values.

Graphs

FIGS. 6-10 show graphs explaining embodiments of inferential relationships for energy content inferences described in the specification. These graphs demonstrate the efficacy of inferring energy content of a flow fluid in a gaseous state based on measurements of the flow fluid in a liquid state.

Natural gas mixtures are typically predominantly composed of methane with smaller relevant quantities of one or more of ethane and propane. Other petroleum substances, such as higher order hydrocarbons and other substances may be present to a lesser extent. Natural gas is typically composed of between 80% and 99% methane with ranges of ethane content varying from 1% to 14%. Because the compositions have these relatively consistent relationships, the inferential relationships can be based on the measurements that are taken in the liquid phase.

The temperature and density for basic alkanes in a liquid state may be largely linearly related. The relationship between viscosity and temperature and the basic alkanes may have more quadratic character. The inferential relationship may use these correlations to infer the energy content of the flow fluid using measurements of the flow fluid that are better associated with the relative composition of the flow fluid than directly derived heat properties of each component. For all of the graphs, the coefficients of the inferential relationships are presumed to have second order temperature dependence, as shown in Eq. (19). It should be appreciated that, despite the embodiments using a second order temperature dependency, embodiments are contemplated where the coefficients are constant values or have temperature dependencies of different orders. Embodiments in which the coefficients are also pressure dependent are considered, however, the pressure effects may be small due to the measurements being conducted on a liquid which is likely marginally compressible.

Figure 6:
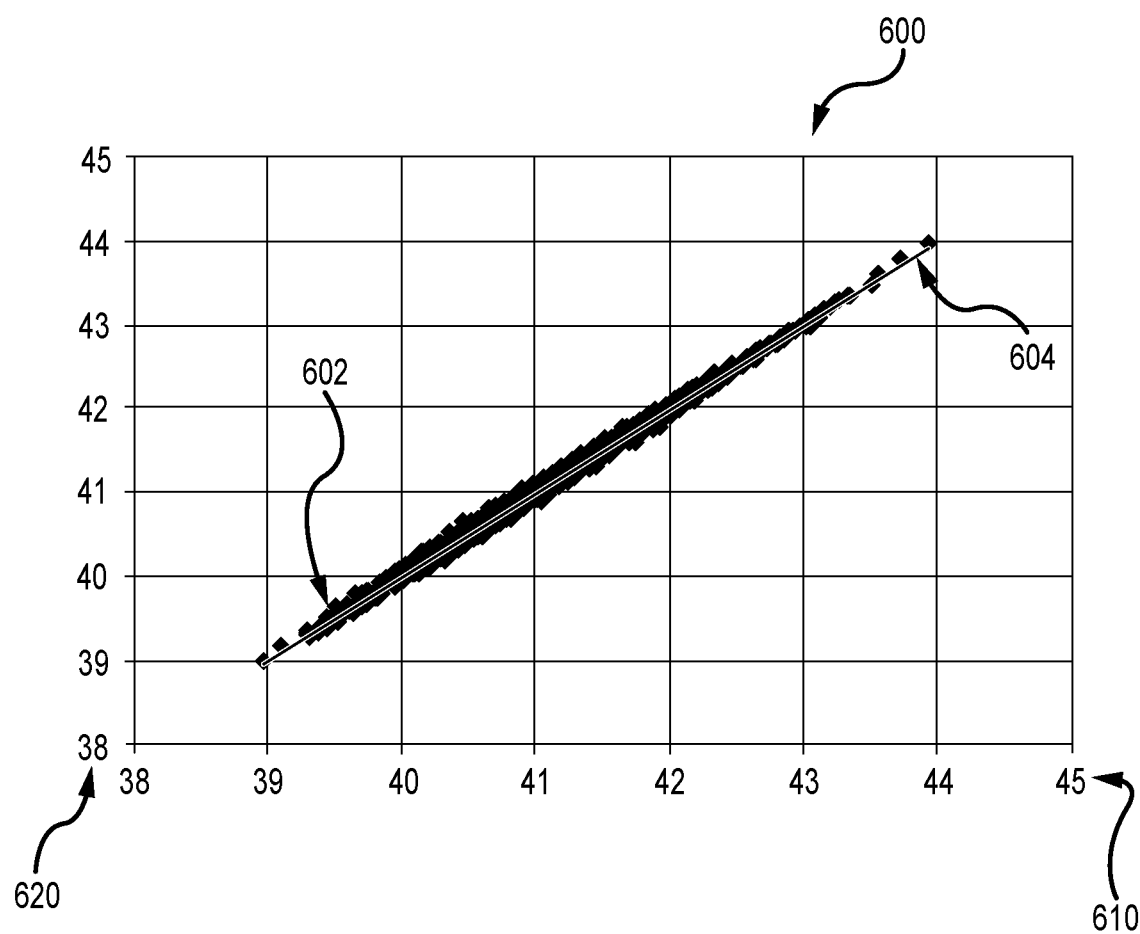
FIG. 6 shows a graph 600 of a fit between measured Wobbe Index values and inferred Wobbe Index values inferred from an embodiment of an inferential relationship.

FIG. 6 shows a graph 600 of a fit between measured Wobbe Index values and inferred Wobbe Index values inferred from an embodiment of an inferential relationship. The graph 600 has a plurality of data points 602 representing relative values of inferred and measured Wobbe Index, a trendline 604, an abscissa 610 representing the measured Wobbe Index of the flow fluid, and an ordinate 620 representing the inferred Wobbe Index of the flow fluid inferred using the inferential relationship.

The embodiment of inferential relationship is a variant of Eq. (17), the inferential relationship represented by Eq. (24):

$$WI_{Gas}=K_1(T)+K_2(T)\times\rho_{liquid}+K_5(T)\times\rho^2_{liquid}+K_4(T)\times\eta_{liquid}+K_6(T)\times\eta^2_{liquid} \quad (24)$$

In Eq. (24), $WI_{Gas}$ is the Wobbe Index of the flow fluid in the gas state, the K values (i.e. $K_1(T)$, $K_2(T)$, $K_5(T)$, $K_4(T)$, $K_6(T)$) are coefficients (temperature dependent in this embodiment), $\rho_{liquid}$ is the density of the flow fluid in a liquid state, and $\eta_{liquid}$ is the viscosity of the flow fluid in a liquid state. It can be seen here that the fit is excellent with a coefficient of determination ($R^2$ value) of 0.996.

Figure 7:
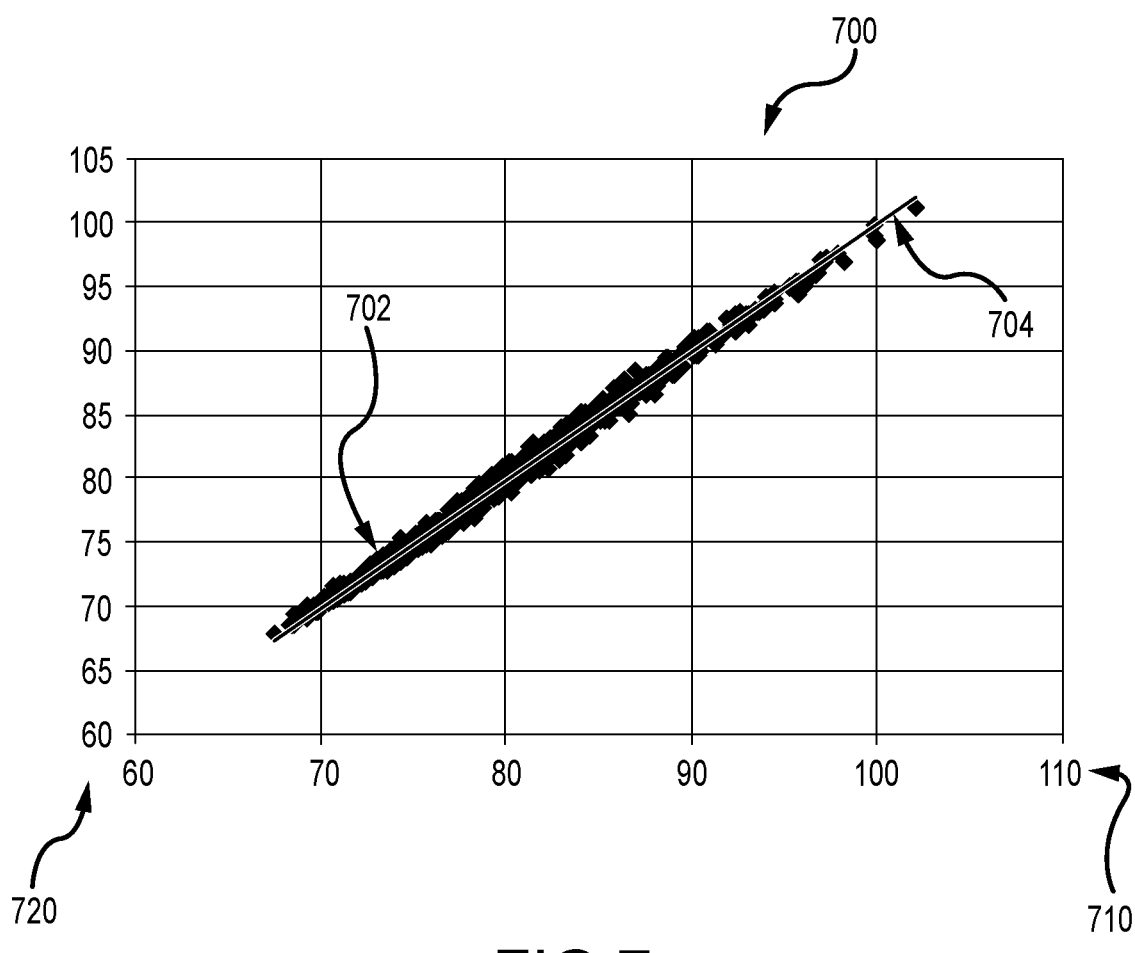
FIG. 7 shows a graph 700 of a fit between measured methane numbers and inferred methane numbers inferred from an embodiment of an inferential relationship.

FIG. 7 shows a graph 700 of a fit between measured methane numbers and inferred methane numbers inferred from an embodiment of an inferential relationship. The graph 700 has a plurality of data points 702 representing relative values of inferred and measured methane number, a trendline 704, an abscissa 710 representing the measured methane number of the flow fluid, and an ordinate 720 representing the inferred methane number of the flow fluid inferred using the inferential relationship.

The embodiment of inferential relationship is a variant of Eq. (17), the inferential relationship represented by Eq. (25):

$$MN_{Gas}=K_1(T)+K_2(T)\times\rho_{liquid}+K_5(T)\times\rho^2_{liquid}+K_4(T)\times\eta_{liquid}+K_6(T)\times\eta^2_{liquid} \quad (25)$$

In Eq. (25), $MN_{Gas}$ is the methane number of the flow fluid in the gas state, the K values (i.e. $K_1(T)$, $K_2(T)$, $K_5(T)$, $K_4(T)$, $K_6(T)$) are coefficients (temperature dependent in this embodiment), $\rho_{liquid}$ is the density of the flow fluid in a liquid state, and $\eta_{liquid}$ is the viscosity of the flow fluid in a liquid state. It can be seen here that the fit is excellent with a coefficient of determination ($R^2$ value) of 0.994.

Figure 8:
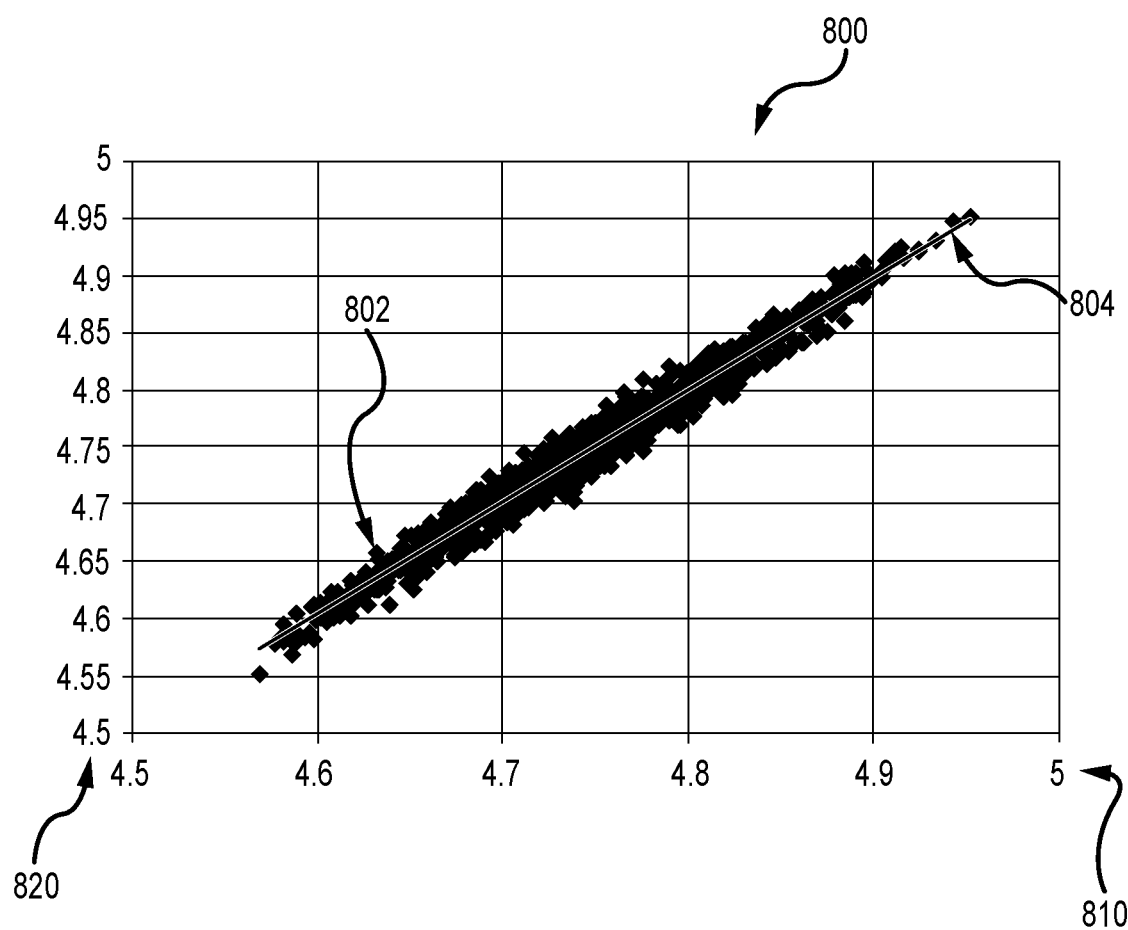
FIG. 8 shows a graph 800 of a fit between measured lower flammability limit and inferred lower flammability limit inferred from an embodiment of an inferential relationship.

FIG. 8 shows a graph 800 of a fit between measured lower flammability limit and inferred lower flammability limit inferred from an embodiment of an inferential relationship. The graph 800 has a plurality of data points 802 representing relative values of inferred and measured lower flammability limit, a trendline 804, an abscissa 810 representing the measured lower flammability limit of the flow fluid, and an ordinate 820 representing the inferred lower flammability limit of the flow fluid inferred using the inferential relationship.

The embodiment of inferential relationship is a variant of Eq. (17), the inferential relationship represented by Eq. (26):

$$LFL_{Gas}=K_1(T)+K_2(T)\times\rho_{liquid}+K_5(T)\times\rho^2_{liquid}+K_4(T)\times\eta_{liquid}+K_6(T)\times\eta^2_{liquid} \quad (26)$$

In Eq. (26), $LFL_{Gas}$ is the lower flammability limit of the flow fluid in the gas state, the K values (i.e. $K_1(T)$, $K_2(T)$, $K_5(T)$, $K_4(T)$, $K_6(T)$) are coefficients (temperature dependent in this embodiment), $\rho_{liquid}$ is the density of the flow fluid in a liquid state, and $\eta_{liquid}$ is the viscosity of the flow fluid in a liquid state. It can be seen here that the fit is excellent with a coefficient of determination ($R^2$ value) of 0.978.

Figure 9:
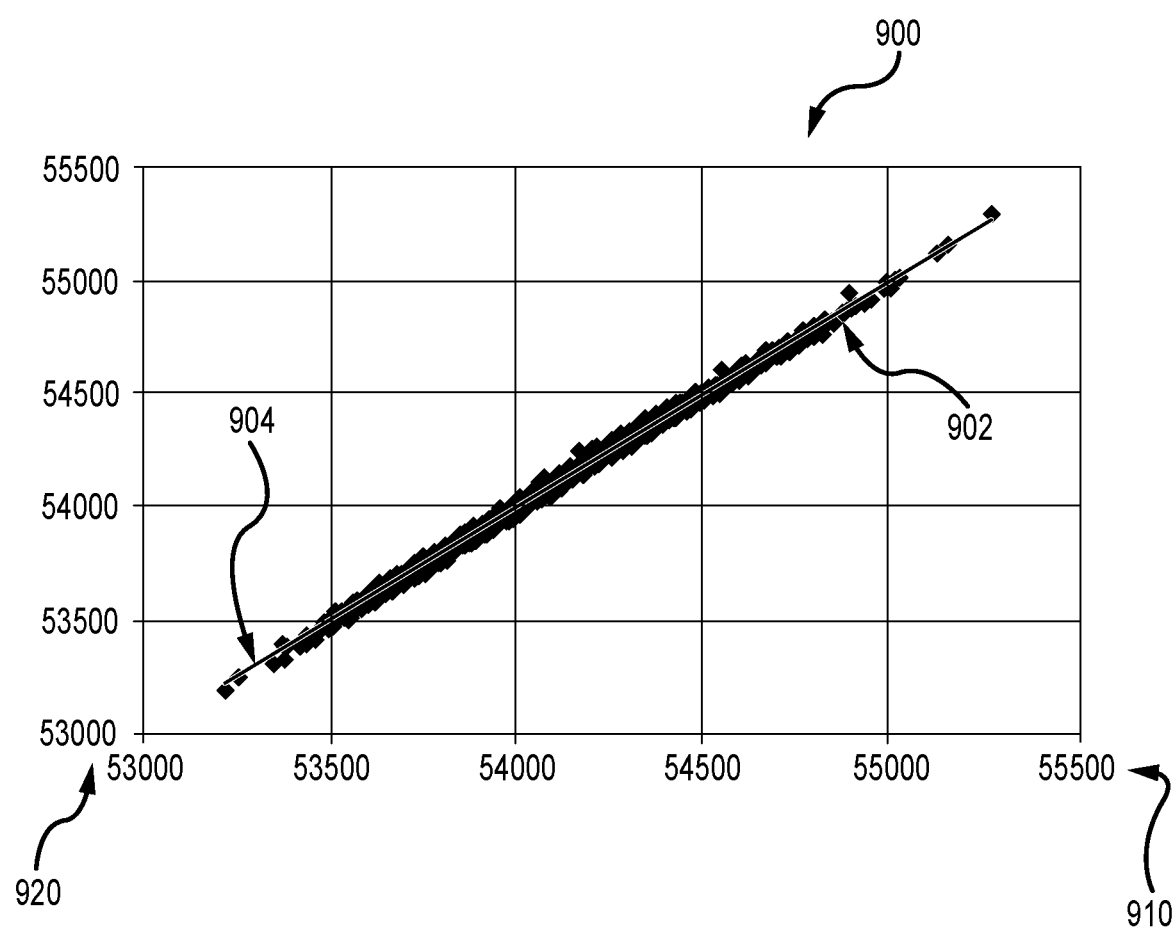
FIG. 9 shows a graph 900 of a fit between measured gross heating value and inferred gross heating value inferred from an embodiment of an inferential relationship.

FIG. 9 shows a graph 900 of a fit between measured gross heating value and inferred gross heating value inferred from an embodiment of an inferential relationship. The graph 900 has a plurality of data points 902 representing relative values of inferred and measured gross heating value, a trendline 904, an abscissa 910 representing the measured gross heating value of the flow fluid, and an ordinate 920 representing the inferred gross heating value of the flow fluid inferred using the inferential relationship.

The embodiment of inferential relationship is a variant of Eq. (17), the inferential relationship represented by Eq. (27):

$$GHV_{Gas}=K_1(T)+K_2(T)\times\rho_{liquid}+K_5(T)\times\rho^2_{liquid}+K_4(T)\times\eta_{liquid}+K_6(T)\times\eta^2_{liquid} \quad (27)$$

In Eq. (27), $GHV_{Gas}$ is the gross heating value of the flow fluid in the gas state, the K values (i.e. $K_1(T)$, $K_2(T)$, $K_5(T)$, $K_4(T)$, $K_6(T)$) are coefficients (temperature dependent in this embodiment), $\rho_{liquid}$ is the density of the flow fluid in a liquid state, and $\eta_{liquid}$ is the viscosity of the flow fluid in a liquid state. It can be seen here that the fit is excellent with a coefficient of determination ($R^2$ value) of 0.997.

Figure 10:
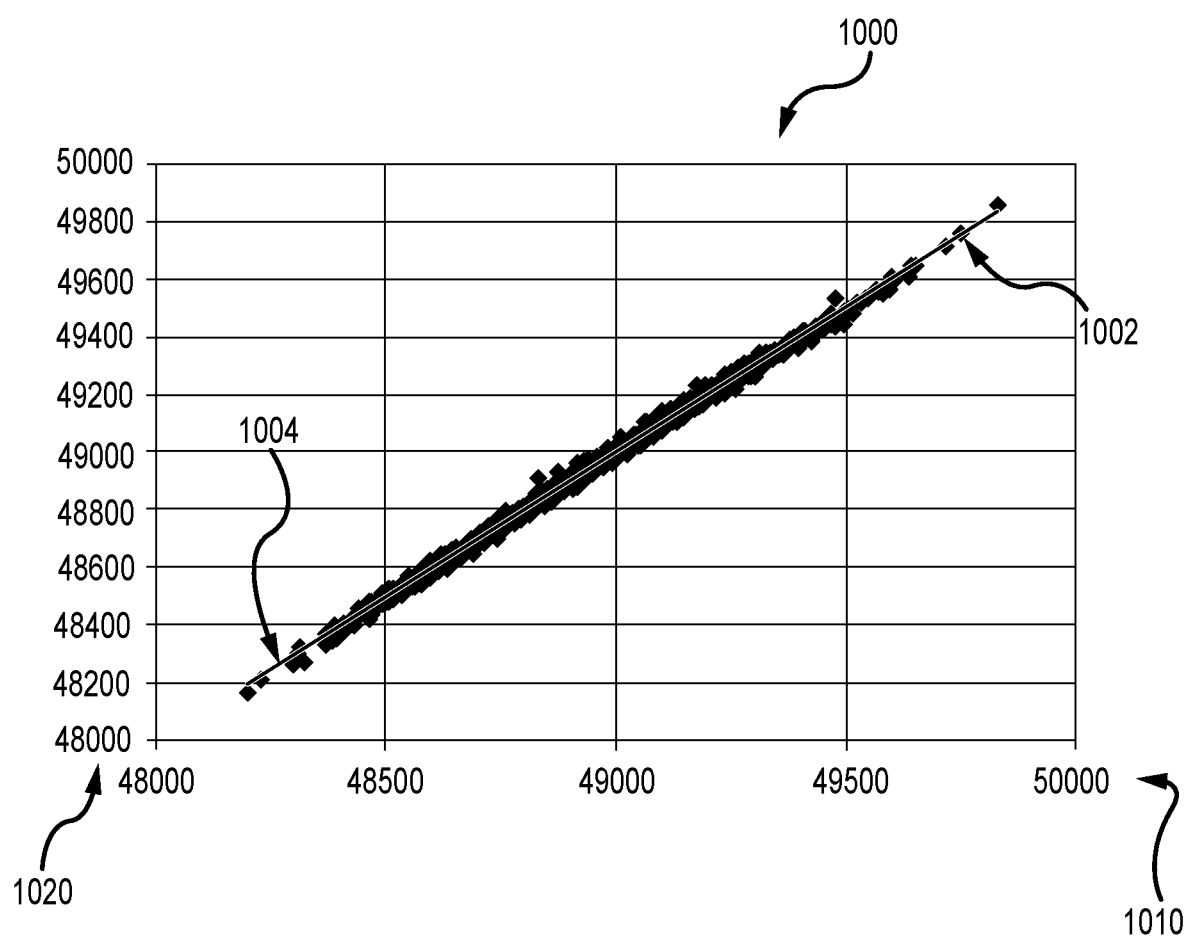
FIG. 10 shows a graph 1000 of a fit between measured net heating value and inferred net heating value inferred from an embodiment of an inferential relationship.

FIG. 10 shows a graph 1000 of a fit between measured net heating value and inferred net heating value inferred from an embodiment of an inferential relationship. The graph 1000 has a plurality of data points 1002 representing relative values of inferred and measured net heating value, a trendline 1004, an abscissa 1010 representing the measured net heating value of the flow fluid, and an ordinate 1020 representing the inferred net heating value of the flow fluid inferred using the inferential relationship.

The embodiment of inferential relationship is a variant of Eq. (17), the inferential relationship represented by Eq. (28):

$$NHV_{Gas}=K_1(T)+K_2(T)\times\rho_{liquid}+K_5(T)\times\rho^2_{liquid}+K_4(T)\times\eta_{liquid}+K_6(T)\times\eta^2_{liquid} \quad (28)$$

In Eq. (28), $NHV_{Gas}$ is the net heating value of the flow fluid in the gas state, the K values (i.e. $K_1(T)$, $K_2(T)$, $K_5(T)$, $K_4(T)$, $K_6(T)$) are coefficients (temperature dependent in this embodiment), $\rho_{liquid}$ is the density of the flow fluid in a liquid state, and $\eta_{liquid}$ is the viscosity of the flow fluid in a liquid state. It can be seen here that the fit is excellent with a coefficient of determination ($R^2$ value) of 0.997.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description. When specific numbers representing parameter values are specified, the ranges between all of those numbers as well as ranges above and ranges below those numbers are contemplated and disclosed.

Thus, although specific embodiments are described herein for illustrative purposes, various equivalent modifications are possible within the scope of the present description, as those skilled in the relevant art will recognize. The teachings provided herein can be applied to other methods and apparatuses for inferring calorific value of a fluid in a gaseous state from measurements taken of the fluid in a liquid state, and not just to the embodiments described above and shown in the accompanying figures. Accordingly, the scope of the embodiments described above should be determined from the following claims.

We claim:

1. A method for determining an energy content of a fluid in its gaseous state, comprising:
   providing a vibratory sensor (102);
   flowing a fluid in its liquid state through the vibratory sensor (102);
   measuring at least one measurement of the fluid in its liquid state with the vibratory sensor (102), wherein the at least one measurement comprises a measured density, a measured speed of sound, and a measured viscosity;

providing meter electronics (110) in communication with the vibratory sensor (102);

providing a computer system (200) of the meter electronics (110) having a processor (210) and memory (220), wherein the memory (220) comprises an inference module (204);

determining, by the inference module (204), an inferred energy content of the fluid in its gaseous state from an inferential relationship between the inferred energy content of the fluid in its gaseous state and the at least one measurement taken, by the vibratory sensor (102), of the fluid in its liquid state, wherein no measurements are taken of the fluid in its gaseous state;

wherein the inferential relationship is a sum of terms, wherein each term has one or more of one of the at least one measurement and one higher order value of one of the at least one measurement wherein each term has a coefficient that corresponds to the term, and wherein the relationship has at least five terms, the at least five terms comprising:

a shift term;

a density term comprising a product of the measured density and the coefficient that corresponds to the density term;

a speed of sound term comprising a product of the measured speed of sound and the coefficient that corresponds to the speed of sound term;

a viscosity term comprising a product of the measured viscosity and the coefficient that corresponds to the viscosity term; and at least one of a higher order viscosity term, a higher order speed of sound term, and a higher order density term, correspondingly comprising a higher order value of the one or more measured viscosity, measured speed of sound, and measured density.

2. The method as claimed in claim 1, wherein each coefficient is temperature dependent, wherein each coefficient temperature dependency has at least one term-specific coefficient constant.

3. The method as claimed in claim 1, wherein the fluid is a natural gas mixture.

4. The method as claimed in claim 1, wherein the energy content is one of methane number, lower flammability limit, Wobbe Index, gross heating value, and net heating value.

5. An apparatus for determining an energy content of a fluid in its gaseous state from at least one measurement taken of the fluid in its liquid state the apparatus, comprising:

a vibratory sensor;

meter electronics (110) comprising;

a processor (210) and memory (220); and an inference module (204) of the memory (220);

wherein the inference module (204) is configured to determine the inferred energy content of the fluid in its gaseous state from an inferential relationship between the inferred energy content of the fluid in its gaseous state with the at least one measurement taken, by the vibratory sensor (102), of the fluid in its liquid state, wherein no measurements are taken of the fluid in its gaseous state;

wherein the inferential relationship is a sum of terms, wherein each term has one or more of one of the at least one measurement and one higher order value of one of the at least one measurement and each term has a coefficient that corresponds to the term, wherein each coefficient is temperature dependent, wherein each coefficient temperature dependency has at least one term-specific coefficient constant, and wherein the relationship has at least five terms, the at least five terms comprising:

a shift term;

a density term comprising the measured density;

a speed of sound term comprising the measured speed of sound;

a viscosity term comprising the measured viscosity; and at least one of a higher order viscosity term, a higher order speed of sound term, and a higher order density term, correspondingly comprising a higher order value of the one or more measured viscosity, measured speed of sound, and measured density.

6. The apparatus as claimed in claim 5, wherein the fluid is a natural gas mixture.

7. The apparatus as claimed in claim 5, wherein the energy content is one of methane number, lower flammability limit, Wobbe Index, gross heating value, and net heating value.

* * * * *